United States Patent [19]
Yoshioka et al.

[11] Patent Number: 5,338,855
[45] Date of Patent: Aug. 16, 1994

[54] THIAZOLIDINE COMPOUNDS CONTAINING A QUINONE GROUP, THEIR PREPARATION AND THEIR THERAPEUTIC USES

[75] Inventors: Takao Yoshioka; Takahide Nishi; Tsutomu Kanai; Yuichi Aizawa; Kunio Wada; Takashi Fujita; Hiroyoshi Horikoshi, all of Tokyo, Japan

[73] Assignee: Sankyo Company, Limited, Tokyo, Japan

[21] Appl. No.: 997,210

[22] Filed: Dec. 28, 1992

[30] Foreign Application Priority Data

Dec. 26, 1991 [JP] Japan ................... 3-344570

[51] Int. Cl.$^5$ ................... C07D 277/34; A01K 31/425
[52] U.S. Cl. ................... 514/369; 548/183
[58] Field of Search ................... 548/183; 514/369

[56] References Cited

U.S. PATENT DOCUMENTS

| | | | |
|---|---|---|---|
| 4,572,912 | 2/1986 | Yoshioka et al. | 514/369 |
| 4,725,010 | 2/1988 | Meguro | 514/369 |
| 5,120,754 | 6/1992 | Clark | 514/369 |
| 5,130,379 | 7/1992 | Clark | 514/333 |
| 5,143,930 | 9/1992 | Yoshioka et al. | 514/369 |

FOREIGN PATENT DOCUMENTS

| | | |
|---|---|---|
| 0008203 | 2/1980 | European Pat. Off. . |
| 0139421 | 5/1985 | European Pat. Off. . |
| 397453 | 11/1990 | European Pat. Off. ............ 514/369 |
| 0441605 | 8/1991 | European Pat. Off. . |

*Primary Examiner*—Robert Gerstl
*Attorney, Agent, or Firm*—Frishauf, Holtz, Goodman & Woodward

[57] ABSTRACT

Compounds of formula (I):

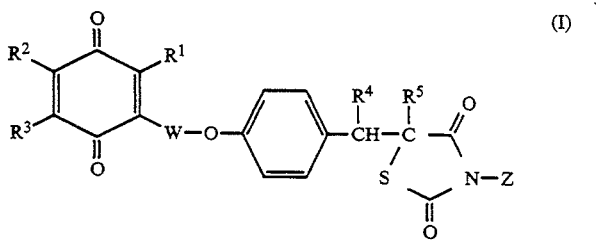

(wherein: $R^1$ is alkyl; $R^2$ and $R^3$ are each alkyl or alkoxy, or $R^2$ and $R^3$ together form an optionally substituted benzene ring and, when $R^2$ and $R^3$ together form said benzene ring, $R^1$ is hydrogen, halogen or alkyl; $R^4$ and $R^5$ both represent hydrogen, or together represent a single carbon-carbon bond; W is a single bond or alkylene; and Z is a hydrogen atom or a cation) have valuable therapeutic and prophylactic activities, including anti-diabetic activities.

29 Claims, No Drawings

THIAZOLIDINE COMPOUNDS CONTAINING A QUINONE GROUP, THEIR PREPARATION AND THEIR THERAPEUTIC USES

BACKGROUND TO THE INVENTION

The present invention relates to a series of thiazolidine derivatives which are characterised by the presence, inter alia, of a quitone group in their molecules. These compounds have valuable therapeutic and prophylactic activities, including anti-diabetic activities, and the invention therefore also provides methods and compositions using these compounds for the treatment and prophylaxis of diabetes and diabetic complications, as described in greater detail hereafter. The invention also provides processes for preparing these novel compounds.

A number of compounds in which a substituted alkoxy-benzyl group is attached to the 5-position of a thiazolidine-2,4-dione group is known. These compounds can be generally represented by the formula (A):

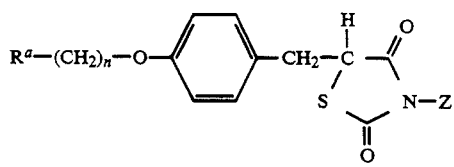

For example, European Patent Publication No. 8 203 discloses a series of compounds of the type shown in formula (A) in which $R^a$ may be an alkyl or cycloalkyl group. European Patent Publication No. 139 421 discloses such compounds in which the group equivalent to $R^a$ in formula (A) above is a chroman or similar group, and Y. Kawamatsu et al. [Chem. Pharm. Bull., 30, 3580–3600 (1982)] disclose a wide range of such compounds of formula (A) in which $R^a$ may be various phenyl, substituted phenyl, alkylamino, cycloalkyl, terpenyl and heterocyclic groups.

All of the prior thiazolidine derivatives referred to above are said to have the ability to lower blood glucose levels, and it is thought that this is achieved by reducing insulin resistance in the peripheral system.

However, it is currently thought that the compounds of the prior art which are closest to those of the present invention are disclosed in European Patent Publication No. 441 605, assigned to the present assignees, as these, like the compounds of the present invention may contain a quinone group, although attached in a different manner to the alkylene group of formula —$(CH_2)_n$—.

We have now discovered a series of novel compounds which, in addition to the ability to reduce insulin resistance in the peripheral tissues (which is the sole basis of the antidiabetic activity of most of the prior art compounds) also exhibits other activities, for example, like the compounds of European Patent Publication No. 441 605, the present compounds have the ability to suppress hepatic gluconeogenesis in the liver, which is one of the causes of diabetes. These additional activities, combined with a low toxicity, mean that the compounds of the present invention will be more effective than the prior art compounds and able to treat a wider range of disorders. The compounds of the present invention have been surprisingly found to have a substantially better activity than do the compounds of prior art European Patent Publication No. 441 605.

BRIEF SUMMARY OF INVENTION

Thus, it is an object of the present invention to provide a series of novel thiazolidine compounds having benzoquinonyl or naphthoquinonyl groups.

It is a further object of the present invention to provide such compounds which have useful therapeutic activities such as anti-diabetic activities.

Other objects and advantages will become apparent as the description proceeds.

Accordingly, the compounds of the present invention are those compounds of formula (I):

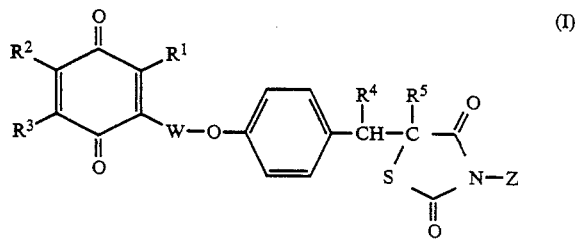

wherein:

$R^1$ represents an alkyl group having from 1 to 5 carbon atoms;

$R^2$ and $R^3$ are the same or different and each represents an alkyl group having from 1 to 5 carbon atoms or an alkoxy group having from 1 to 5 carbon atoms, or $R^2$ and $R^3$ together form a benzene ring which is unsubstituted or which is substituted by at least one substituent selected from the group consisting of substituents A, defined below, and, when $R^2$ and $R^3$ together form said benzene ring, $R^1$ represents a hydrogen atom, a halogen atom or an alkyl group having from 1 to 5 carbon atoms;

$R^4$ and $R^5$ both represent hydrogen atoms, or $R^4$ and $R^5$ together represent a single carbon-carbon bond (to form a double bond between the two carbon atoms to which they are shown as attached);

W represents a single bond or an alkylene group having from 1 to 5 carbon atoms; and Z represents a hydrogen atom or a 1/x equivalent of a cation, where x is the charge on the cation; and substituents A are selected from the group consisting of alkyl groups having from 1 to 5 carbon atoms, alkoxy groups having from 1 to 5 carbon atoms and halogen atoms.

The invention also provides a pharmaceutical composition for the treatment or prophylaxis of diabetes or hyperlipemia, which comprises an effective amount of an active compound in admixture with a pharmaceutically acceptable carrier or diluent, wherein said active compound is selected from the group consisting of compounds of formula (I), defined above.

The invention still further provides a method for the treatment or prophylaxis of diabetes or hyperlipemia in a mammal, which may be human, which method comprises administering to said mammal an effective amount of an active compound, wherein said active compound is selected from the group consisting of compounds of formula (I), defined above.

The invention also provides processes for the preparation of the compounds of the present invention, which processes are described in more detail hereafter.

DETAILED DESCRIPTION OF INVENTION

In the compounds of the present invention, where $R^1$, $R^2$ or $R^3$ represents an alkyl group, this may be a straight or branched chain alkyl group having from 1 to 5 carbon atoms, and examples include the methyl, ethyl, propyl, isopropyl, butyl, isobutyl, sec-butyl, t-butyl, pentyl, neopentyl and isopentyl groups. Of these, we prefer those alkyl groups having from 1 to 4 carbon atoms, most preferably the methyl group.

Where $R^2$ and $R^3$ together form a benzene ring (that is, the benzene ring forms, with the ring to which it is fused, a naphthoquinone system), this may be unsubstituted or it may have, on the ring portion represented by $R^2$ and $R^3$, one or more substituents selected from the group consisting of substituents A, as exemplified below. In addition, in this case, $R^1$, may represent a hydrogen atom, a halogen atom, or one of the alkyl groups exemplified above. Also, in this case, substituents A may be selected from the group consisting of alkyl groups having from 1 to 5 carbon atoms, such as those exemplified above, alkoxy groups having from 1 to 5 carbon atoms and halogen atoms.

Where the resulting fused benzene ring is substituted, there is no particular limitation on the number of substituents, except such as may be imposed by the number of substitutable positions or possibly by steric constraints. In general, from 1 to 4 substituents are possible, although fewer are preferred, from 1 to 3 being generally more preferred, and 1 or 2 being still more preferred. We most prefer no substituents on this fused benzene ring.

Where $R^2$, $R^3$ or substituent A represents an alkoxy group, this may be a straight or branched chain alkoxy group having from 1 to 5 carbon atoms, and examples include the methoxy, ethoxy, propoxy, isopropoxy, butoxy, isobutoxy, sec-butoxy, t-butoxy, pentyloxy, neopentyloxy and isopentyloxy groups. Of these, we prefer those alkoxy groups having from 1 to 4 carbon atoms, most preferably the methoxy group.

Where $R^1$ or substituent A represents a halogen atom, this may be, for example, a chlorine, fluorine or bromine atom, preferably a chlorine or fluorine atom, and most preferably a chlorine atom.

W may represent a single bond or an alkylene group. Where W represents an alkylene group, this may be a straight or branched chain alkylene group having from 1 to 5 carbon atoms. The bonds of the alkylene group by which it is attached, on the one hand, to the benzoquinone or naphthoquinone group and, on the other hand, to the oxygen atom may be on the same carbon atoms or on different carbon atoms. Where the bonds are on the same carbon atoms, the groups are sometimes referred to as "alkylidene groups". It is, however, conventional to use the general term "alkylene group" to include both those groups where the bonds are on the same carbon atom and those where they are on different carbon atoms. Examples of such groups include the methylene, ethylene, trimethylene, tetramethylene, pentamethylene, methylmethylene, 2,2-dimethyltrimethylene, 2-ethyltrimethylene, 1-methyltetramethylene, 2-methyltetramethylene and 3-methyltetramethylene groups, of which we prefer those alkylene groups (which may be straight or branched chain groups) having from 1 to 4 carbon atoms, and most prefer the straight chain alkylene groups having 2 or 3 carbon atoms.

Z may represent a hydrogen atom or a cation. Where the cation has a plural charge, for example 2+, then Z represents a number of equivalents of that cation which is the reciprocal of that charge. For example, where Z represents an alkali metal, examples of such alkali metals include lithium, sodium or potassium, and the charge borne by these metals being 1+, Z represents, for each equivalent of the compound of formula (I), one equivalent of the metal. Where Z represents an alkaline earth metal, examples of such alkaline earth metals include calcium or barium, and the charge borne by these metals being 2+, Z represents, for each equivalent of the compound of formula (I), one half equivalent of the metal. Where Z represents a basic amino acid, examples of such amino acids include lysine or arginine, and the charge borne by these acids being 1+, Z represents, for each equivalent of the compound of formula (I), one equivalent of the acid.

Preferably Z represents an alkali metal, one half equivalent of an alkaline earth metal or a basic amino acid.

The compounds of the present invention necessarily contain at least one asymmetric carbon at the 5-position of the thiazolidine ring, and, depending on the nature of the groups and atoms represented by $R^1$, $R^2$, $R^3$ and W, may contain several asymmetric carbon atoms in their molecules. They can thus form optical isomers. They can also form tautomers due to the interconversion of the imide group formed by the oxo groups at the 2- and 4-positions of the thiazolidine ring to a group of formula —N=C(OH)—. Although these optical isomers and tautomers are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

A preferred class of compounds of the present invention are those compounds of formula (I) in which:

$R^1$ represents an alkyl group having from 1 to 5 carbon atoms;

$R^2$ and $R^3$ are the same or different, particularly preferably the same, and each represents an alkyl group having from 1 to 5 carbon atoms or an alkoxy group having from 1 to 5 carbon atoms, or $R^2$ and $R^3$ together form an unsubstituted benzene ring, and, when $R^2$ and $R^3$ together form said benzene ring, $R^1$ represents a hydrogen atom, a methyl group or a chlorine atom, more preferably a hydrogen atom;

$R^4$ and $R^5$ each represents a hydrogen atom;

W represents an alkylene group having from 1 to 5 carbon atoms; and

Z represents a hydrogen atom or a sodium atom.

A more preferred class of compounds of the present invention are those compounds of formula (I) in which:

$R^1$ represents an alkyl group having from 1 to 5 carbon atoms:

$R^2$ and $R^3$ are the same or different and each represents an alkyl group having from 1 to 5 carbon atoms:

$R^4$ and $R^5$ each represents a hydrogen atom;

W represents an alkylene group having 2 to 4 carbon atoms; and

Z represents a hydrogen atom or a sodium atom.

The most preferred class of compounds of the present invention are those compounds of formula (I) in which:

$R^1$, $R^2$ and $R^3$ each represents a methyl group;
$R^4$ and $R^5$ each represents a hydrogen atom;
W represents an ethylene or trimethylene group; and
Z represents a hydrogen atom or a sodium atom.

Specific examples of compounds of the invention are those compounds having the following formulae (I-1) to (I-3), in which the substituents are as defined in the respective one of Tables 1 to 3, i.e. Table 1 relates to formula (I-1), Table 2 relates to formula (I-2), and Table 3 relates to formula (I-3). In the Tables the following abbreviations are used for certain groups; otherwise, standard internationally recognised symbols are used to designate atoms:

| | |
|---|---|
| Bu | butyl |
| Et | ethyl |
| Me | methyl |

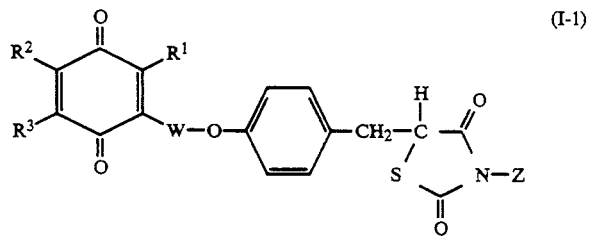

(I-1)

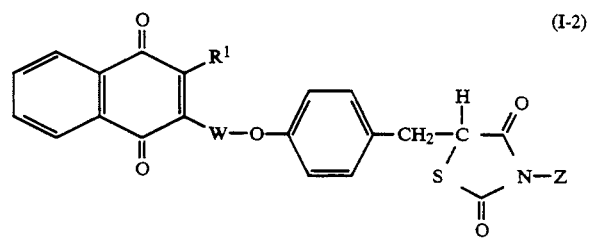

(I-2)

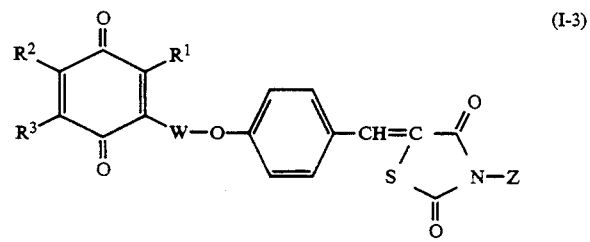

(I-3)

TABLE 1

| Cpd. No. | $R^1$ | $R^2$ | $R^3$ | W | Z |
|---|---|---|---|---|---|
| 1-1 | Me | Me | Me | single bond | H |
| 1-2 | Me | Me | Me | single bond | Na |
| 1-3 | Me | Me | M | —CH$_2$— | H |
| 1-4 | M | Me | Me | —CH$_2$— | Na |
| 1-5 | Me | Me | Me | —(CH$_2$)$_2$— | H |
| 1-6 | Me | Me | Me | —(CH$_2$)$_2$— | Na |
| 1-7 | Me | Me | Me | —(CH$_2$)$_3$— | H |
| 1-8 | Me | Me | Me | —(CH$_2$)$_3$— | Na |
| 1-9 | Me | Me | Me | —(CH$_2$)$_4$— | H |
| 1-10 | Me | Me | Me | —(CH$_2$)$_4$— | Na |
| 1-11 | Me | Et | Et | —(CH$_2$)$_2$— | Na |
| 1-12 | Me | Bu | Bu | —(CH$_2$)$_3$— | Na |
| 1-13 | Me | MeO | MeO | single bond | H |
| 1-14 | Me | MeO | MeO | single bond | Na |
| 1-15 | Me | MeO | MeO | —CH$_2$— | H |
| 1-16 | Me | MeO | MeO | —CH$_2$— | Na |
| 1-17 | Me | MeO | MeO | —(CH$_2$)$_2$— | H |

TABLE 1-continued

| Cpd. No. | $R^1$ | $R^2$ | $R^3$ | W | Z |
|---|---|---|---|---|---|
| 1-18 | Me | MeO | MeO | —(CH$_2$)$_2$— | Na |
| 1-19 | Me | MeO | MeO | —(CH$_2$)$_3$— | H |
| 1-20 | Me | MeO | MeO | —(CH$_2$)$_3$— | Na |
| 1-21 | Me | MeO | MeO | —(CH$_2$)$_4$— | H |
| 1-22 | Me | MeO | MeO | —(CH$_2$)$_4$— | Na |

TABLE 2

| Cpd. No. | $R^1$ | W | Z |
|---|---|---|---|
| 2-1 | H | single bond | H |
| 2-2 | H | single bond | Na |
| 2-3 | H | —CH$_2$— | H |
| 2-4 | H | —CH$_2$— | Na |
| 2-5 | H | —(CH$_2$)$_2$— | H |
| 2-6 | H | —(CH$_2$)$_2$— | Na |
| 2-7 | H | —(CH$_2$)$_3$— | H |
| 2-8 | H | —(CH$_2$)$_3$— | Na |
| 2-9 | H | —(CH$_2$)$_4$— | H |
| 2-10 | H | —(CH$_2$)$_4$— | Na |
| 2-11 | Me | single bond | H |
| 2-12 | Me | single bond | Na |
| 2-13 | Me | —CH$_2$— | H |
| 2-14 | Me | —CH$_2$— | Na |
| 2-15 | Me | —(CH$_2$)$_2$— | H |
| 2-16 | Me | —(CH$_2$)$_2$— | Na |
| 2-17 | Me | —(CH$_2$)$_3$— | H |
| 2-18 | Me | —(CH$_2$)$_3$— | Na |
| 2-19 | Me | —(CH$_2$)$_4$— | H |
| 2-20 | Cl | single bond | H |
| 2-21 | Cl | single bond | Na |
| 2-22 | Cl | —CH$_2$— | H |
| 2-23 | Cl | —CH$_2$— | Na |
| 2-24 | Cl | —(CH$_2$)$_2$— | H |
| 2-25 | Cl | —(CH$_2$)$_2$— | Na |
| 2-26 | Cl | —(CH$_2$)$_3$— | H |
| 2-27 | Cl | —(CH$_2$)$_3$— | Na |
| 2-28 | Cl | —(CH$_2$)$_4$— | H |
| 2-29 | H | —(CH$_2$)$_5$— | H |
| 2-30 | H | —CH$_2$—C(CH$_3$)$_2$—CH$_2$— | H |
| 2-31 | Me | —CH$_2$—C(CH$_3$)$_2$—CH$_2$— | H |
| 2-32 | Cl | —CH$_2$—C(CH$_3$)$_2$—CH$_2$— | H |

TABLE 3

| Cpd. No. | $R^1$ | $R^2$ | $R^3$ | W | Z |
|---|---|---|---|---|---|
| 3-1 | Me | Me | Me | —(CH$_2$)$_2$— | H |
| 3-2 | Me | Me | Me | —(CH$_2$)$_2$— | Na |
| 3-3 | Me | Me | Me | —(CH$_2$)$_3$— | H |
| 3-4 | Me | Me | Me | —(CH$_2$)$_3$— | Na |
| 3-5 | Me | Me | Me | —(CH$_2$)$_4$— | H |
| 3-6 | Me | Me | Me | —(CH$_2$)$_4$— | Na |
| 3-7 | Me | —CH=CH—CH=CH— | | —(CH$_2$)$_2$— | H |
| 3-8 | Me | —CH=CH—CH=CH— | | —(CH$_2$)$_3$— | H |

Of the compounds listed above, preferred compounds are Compounds Nos.:

1-4.   5-[4-(3,5,6-Trimethyl-1,4-benzoquinon-2-yl-methoxy)benzyl]thiazolidine-2,4-dione sodium salt;

1-5.   5-{4-[2-(3,5,6-Trimethyl-1,4-benzoquinon-2-yl)ethoxy]benzyl}thiazolidine-2,4-dione;

1-7.   5-{4-[3-(3,5,6-Trimethyl-1,4-benzoquinon-2-yl)propoxy]benzyl}thiazolidine-2,4-dione;

1-8.   5-{4-[3-(3,5,6-Trimethyl-1,4-benzoquinon-2-yl)propoxy]benzyl}thiazolidine-2,4-dione sodium salt; and 1-9.   5-{4-[4-(3,5,6-Trimethyl-1,4-benzoquinon-2-yl)butoxy]benzyl}thiazolidine-2,4-dione;

The more preferred compounds are Compounds Nos. 1-5 and 1-8, Compound No. 1-5 being the most preferred.

The compounds of the present invention may be prepared by a variety of processes known for the preparation of this type of compound. For example, in general terms, they may be prepared by oxidizing a compound of formula (II):

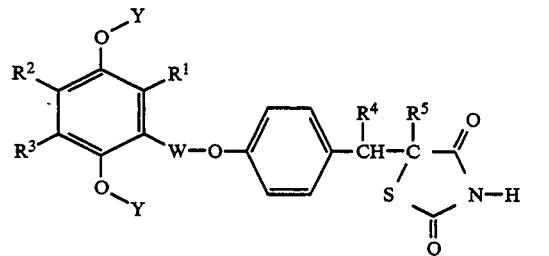

(wherein $R^1$, $R^2$, $R^3$, $R^4$, $R^5$ and W are as defined above, and Y represents a hydrogen atom, an alkyl group having from 1 to 5 carbon atoms, an aliphatic carboxylic acyl group having from 1 to 6 carbon atoms, a carbocyclic aromatic carboxylic acyl group or an alkoxyalkyl group in which each alkyl or alkoxy part has from 1 to 4 carbon atoms), to give a compound of formula (Ia):

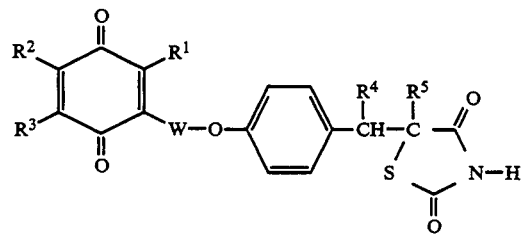

(wherein $R^1$, $R^2$, $R^3$, $R^4$, $R^5$ and W are as defined above) and, where $R^4$ and $R^5$ each represent hydrogen atoms, if desired, oxidizing said compound to give a compound of formula (Ia) in which $R^4$ and $R^5$ together form a single bond, and, if desired, salifying the product.

Where Y represents an alkyl group, this my be a straight or branched chain group having from 1 to 5 carbon atoms, and examples are as given in relation to the alkyl groups which may be represented by $R^1$, preferably a methyl group. Where Y represents an aliphatic carboxylic acyl group, this may be a straight or branched chain group having from 1 to 6 carbon atoms, and examples include the formyl, acetyl, propionyl, butyryl, isobutyryl, valeryl, isovaleryl, pivaloyl and hexanoyl groups, preferably an acetyl group. Where Y represents a carbocyclic aromatic carboxylic acyl group, the aromatic part may have from 6 to 10 carbon atoms in a carbocyclic ring, and examples include the benzoyl and naphthoyl groups. Where Y represents an alkoxyalkyl group, each of the alkyl and the alkoxy parts has from 1 to 4 carbon atoms, and examples include the methoxymethyl, ethoxymethyl, propoxymethyl, butoxymethyl, 2-methoxyethyl, 2-ethoxyethyl, 2-propoxyethyl, 2-butoxyethyl, 3-methoxypropyl and 4-methoxybutyl groups. We particularly prefer that Y should represent a methyl or acetyl group.

Alternatively, the compounds of formula (Ia) in which W represents a single bond and $R^4$ and $R^5$ each represents a hydrogen atom may be prepared by the reaction described hereafter in Reaction Scheme C.

Compounds of formula (II) or salts thereof are of significant value as intermediates in the preparation of compounds of formula (I).

In more detail, the compounds of the present invention may be prepared as illustrated by the following Reaction Schemes A, B, C and D.

Reaction Scheme A

In Reaction Scheme A, a desired compound of formula (1-A) is prepared from an intermediate of formula (2), which may be prepared as illustrated by Reaction Scheme E, F, G or H described later, optionally via an intermediate of formula (3).

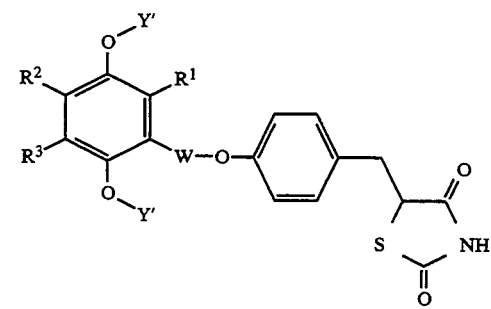

(2)

Step A2

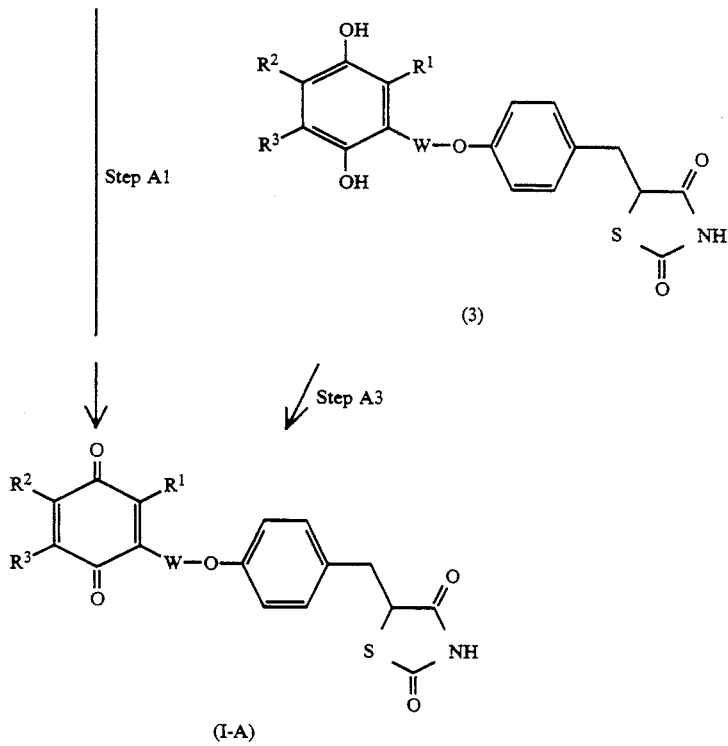

In the above formulae, $R^1$, $R^2$, $R^3$ and W are as defined above, and Y' represents an alkyl group, an acyl group or an alkoxyalkyl group, as defined and exemplified above in relation to Y.

In Step A1 of this reaction scheme, the desired compound of formula (I-A) is prepared by oxidizing an intermediate of formula (2) directly. For example, when Y' in the compound of formula (2) represents a lower alkyl group, particularly a methyl group, the desired compound of formula (I-A) can be prepared by treating the intermediate of formula (2) with ceric ammonium nitrate by the procedure described in Fieser & Fieser, "Reagents for Organic Synthesis", Vol. 7, pp. 55, A Wiley-Interscience Publication, edited by John Wiley & Sons, the disclosure of which is incorporated herein by reference.

The oxidation reaction using cerium ammonium nitrate is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; nitriles, such as acetonitrile; ketones, such as acetone; and mixtures of any two or more of these solvents. There is no particular limitation upon the amount of cerium ammonium nitrate used, but we prefer to use from 1 to 10 moles of cerium ammonium nitrate per mole of the intermediate of formula (2).

The reaction can take place over a wide range of temperatures, and the precise reaction temperature is not critical to the invention. In general, although the preferred temperature will depend on the nature of the starting materials and solvents, we find it convenient to carry out the reaction at a temperature of from −10° to 40° C. The time required for the reaction may also vary widely, depending on many factors, notably the reaction temperature and the nature of the reagents and solvent employed. However, provided that the reaction is effected under the preferred conditions outlined above, a period of from several minutes to several tens of hours will usually suffice.

In Step A2 of this reaction scheme, an intermediate of formula (3) is first prepared from the intermediate of formula (2), and then this is converted into the desired compound of formula (I-A). The conversion of the intermediate of formula (2) into the intermediate of formula (3) may be carried out by, for example, a conventional hydrolysis reaction. Where Y' is, for example, an acetyl or methoxymethyl group, it is hydrolyzed, to give the compound of formula (3), and then the product is submitted to conventional oxidation, for example, air oxidation or oxidation using a metal ion (such as a ferric or cupric ion) or using manganese dioxide, to give the desired compound of formula (I-A). Both of these reactions may be carried out using reagents and reaction conditions which are well known in the art.

Reaction Scheme B

Reaction Scheme B illustrates the preparation of compounds of formula (I-B) in which $R^4$ and $R^5$ together represent a single bond.

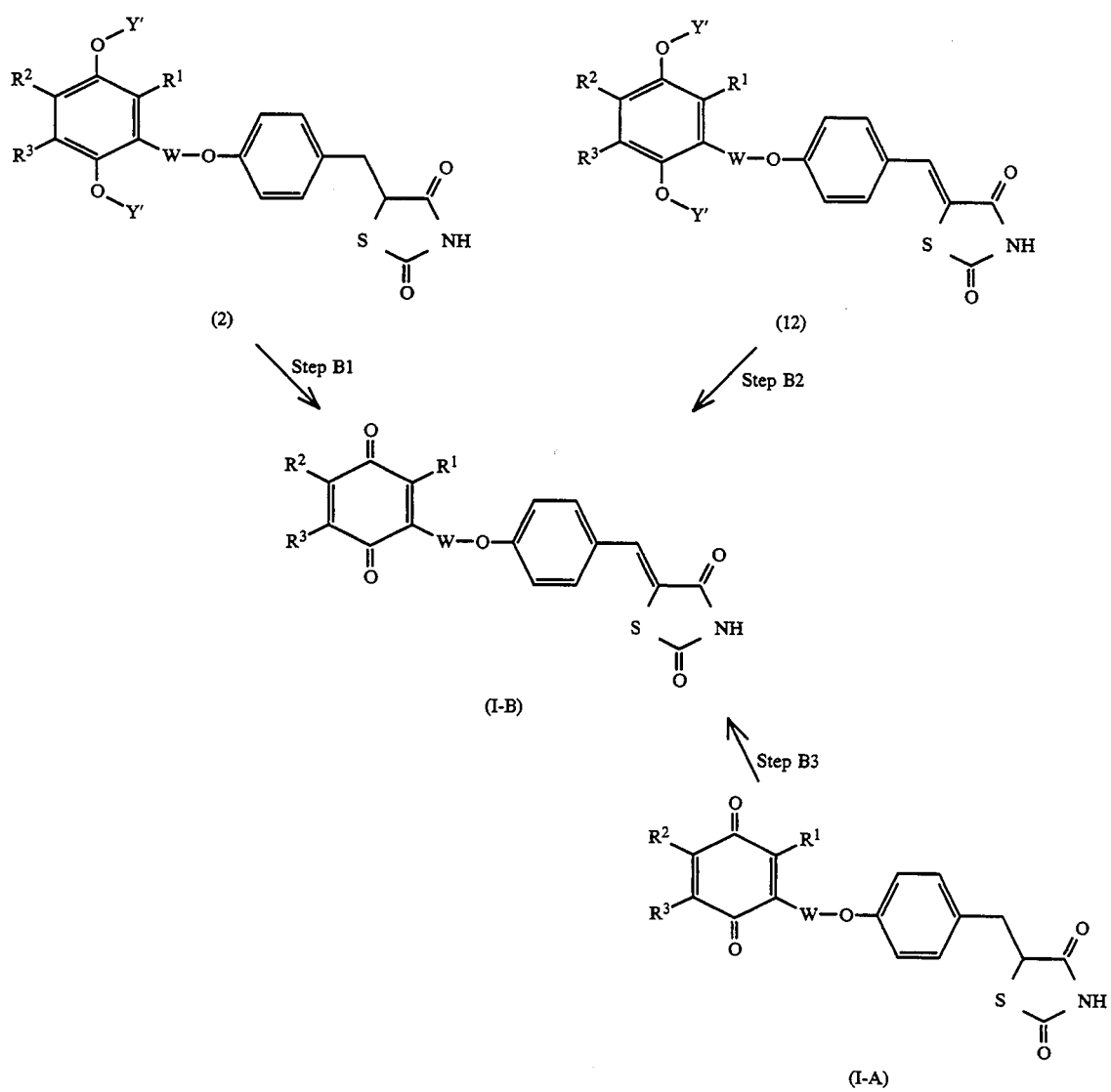

In the above formulae, $R^1$, $R^2$, $R^3$, W and Y' are as defined above.

In Step B1 of this reaction scheme, the desired compounds of formula (I-B) can be prepared by oxidizing a compound of formula (I-A), which may have been prepared as described in Reaction Scheme A, or by oxidizing an intermediate of formula (2) or an intermediate of formula (12), which is described later. These oxidation reactions may, for example, be carried out following the procedure described in Step A1 of Reaction Scheme A, using cerium ammonium nitrate.

Reaction Scheme C

In Reaction Scheme C, the desired compound of formula (I-C), wherein W represents a single bond, can be prepared. The reaction is particularly useful for the preparation of compounds wherein $R^2$ and $R^3$ together form a benzene ring which is unsubstituted or which is substituted as defined above.

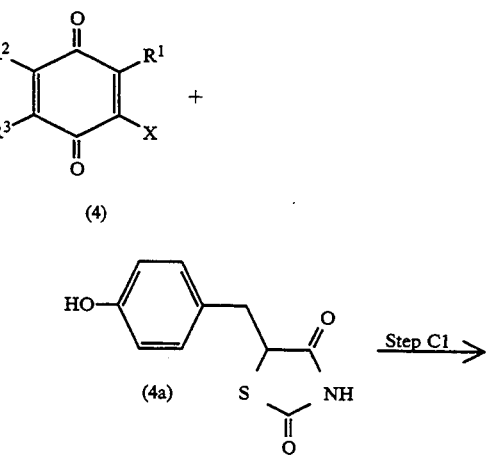

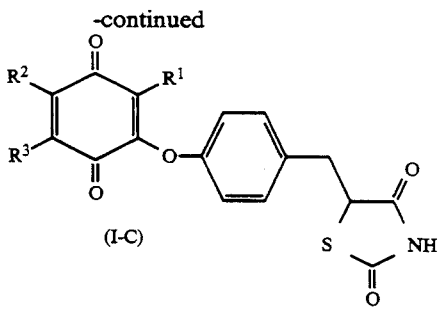

(I-C)

In the above formulae, $R^1$, $R^2$ and $R^3$ are as defined above and X represents a halogen atom, such as a chlorine, bromine or iodine atom.

The reaction is normally and preferably carried out in the presence of a base or by using an alkali metal salt (for example the sodium salt) of the 5-(4-hydroxybenzyl)thiazolidine-2,4-dione of formula (4a). The base and the solvent which may be used for this reaction, as well as the reaction temperature and the time required for the reaction, are similar to those of the procedure of Reaction Scheme G described later.

Alternatively, a compound of formula (4) is reacted with 4-hydroxynitrobenzene or with a salt thereof, to give a 3-halo-2-(4-nitrophenoxy)-1,4-naphthoquinone derivative, and then the product is converted to a compound of formula (5):

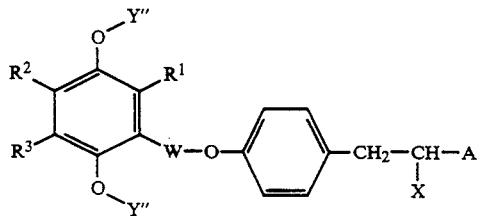

(in which $R^1$, $R^2$, $R^3$ and W are as defined above, Y‴ represents a methyl or acetyl group and A represents a carboxyl, alkoxycarbonyl or carbamoyl group, or a group of formula —COOM) by the procedure of the literature described in Reaction Scheme E, and given hereafter. Examples of alkoxycarbonyl groups which may be represented by A include the methoxycarbonyl, ethoxycarbonyl, isopropoxycarbonyl and butoxycarbonyl groups.

In the group of formula —COOM, M represents a cation, for example, an equivalent cation such as a metal atom (for example sodium, potassium, calcium or aluminium) or an ammonium ion. Subsequently, after carrying out the procedure of Reaction Scheme E, a compound of formula (2) can be prepared from the compound of formula (5). The reaction is carried out under the same condition as those described in Reaction Scheme E. After that, following the procedure described in Reaction Scheme A or B, the desired compound of formula (I) can be prepared from the compound of formula (2).

Reaction scheme D

In Reaction Scheme D, the desired compound of formula (I), for example wherein Z represents a sodium atom, can be prepared in the form of a salt, that is by replacing the hydrogen atom of the imide group with a metal atom by reacting a compound of formula (Ia) with a suitable base by conventional means. There is no particular limitation upon the nature of the base used.

Examples of such bases include: sodium hydroxide, alcoholares, such as sodium methoxide or sodium ethoxide, and sodium salts of organic acids, such as sodium 2-ethylhexanoate. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. The preferred solvent used may vary, depending upon the nature of the base used, but examples of the solvents which may be used include: lower alcohols, such as methanol or ethanol; esters, such as ethyl acetate or propyl acetate; ethers, such as tetrahydrofuran or dioxane; water; and mixtures of any two or more of the above solvents. Salts of other metals, for example potassium or calcium, or the corresponding salts of basic amino acids or other organic bases can be prepared in a similar manner to the preparation of the sodium salts described above.

Reaction Scheme E and the following Reaction Schemes relate to the preparation of an intermediate of formula (2).

Reaction Scheme E

Reaction Scheme E consists of the procedure described in European Patent Publication No. 139 421 (Japanese Patent Kokai Application No. Sho 60-51189 =Japanese Patent Publication No. Hei 2-31079). In this procedure, an intermediate of formula (6):

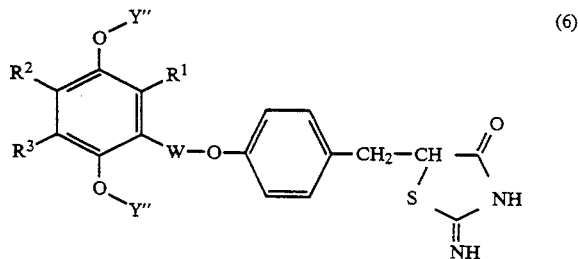

(in which $R^1$, $R^2$, $R^3$, W and Y″ are as defined above) is prepared by reacting a compound of formula (5):

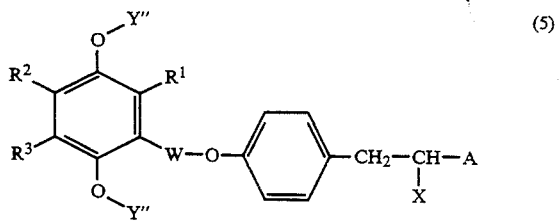

(in which $R^1$, $R^2$, $R^3$, W, X, Y″ and A are as defined above) with thiourea. The compound of formula (5) may be prepared by the procedure of the description concerning α-halocarboxylic acids and/or the "Referential Examples" in the cited patent.

The reaction of the compound of formula (5) with thiourea is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol, butanol or ethylene glycol monomethyl ether; ethers, such as tetrahydrofuran or dioxane; ketones, such as acetone; sulfoxides, such as dimethyl sulfoxide or sulfolane; and amides, such as dimethylformamide or dimethylacetamide. There is no particular limitation upon the molar ratio of the compound of formula (5) to the thiourea used, but the reaction is preferably carried out using at least a slight molar excess of thiourea relative to the compound of formula (5). It is more preferred to use from 1 to 2 moles of thiourea per mole of the compound of formula (5). The reaction can take place over a wide range of temperatures, and the precise reaction temperature is not critical to the invention, although the preferred temperature may vary depending upon the nature of the starting materials and the solvents. In general, we find it convenient to carry out the reaction at a temperature of from 80° to 150° C. The time required for the reaction may also vary widely, depending on many factors, notably the reaction temperature and the nature of the reagents and solvent employed. However, provided that the reaction is effected under the preferred conditions outlined above, a period of from 1 to several tens of hours will usually suffice.

After that, still following the procedure described in the patent cited above, an intermediate of formula (2-1):

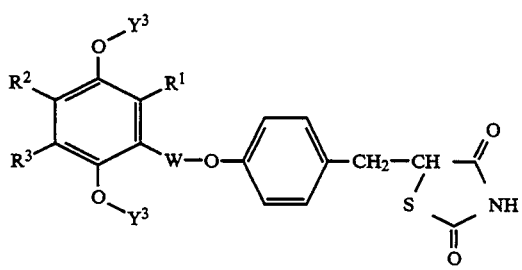

(2-1)

(in which $R^1$, $R^2$, $R^3$ and W are as defined above and $Y^3$ represents a hydrogen atom, a methyl group or an acetyl group) can be prepared by hydrolysis of the compound (6).

This hydrolysis may be carried out by heating the compound of formula (6) in an appropriate solvent (for example sulfolane, methanol, ethanol or ethylene glycol monomethyl ether) in the presence of water and an organic acid, such as acetic acid, or a mineral acid such as sulfuric acid or hydrochloric acid. The amount of the acid is normally and preferably from 0.1 to 10 moles, more preferably from 0.2 to 3 moles, per mole of the intermediate of formula (6). Water or an aqueous solvent is normally added in a large excess relative to the molar amount of the intermediate of formula (6). The reaction can take place over a wide range of temperatures, and the precise reaction temperature is not critical to the invention. In general, we find it convenient to carry out the reaction at a temperature of from 50° to 100° C. The time required for the reaction may also vary widely, depending on many factors, notably the reaction temperature and the nature of the reagents and solvent employed. However, provided that the reaction is effected under the preferred conditions outlined above, a period of from several hours to several tens of hours will usually suffice.

Reaction Scheme F

In this reaction scheme, an intermediate of formula (9) can be prepared by the procedure reported in J. Med. Chem., 1538 (1991).

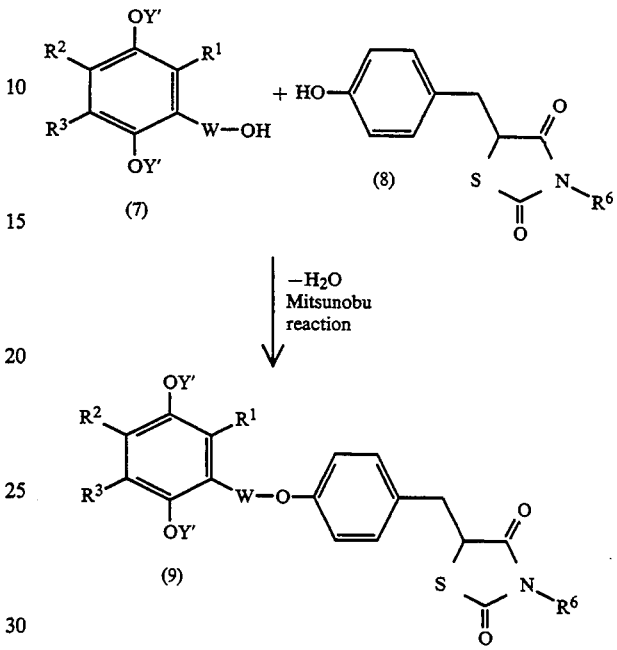

In the above formulae, $R^1$, $R^2$, $R^3$, W and Y' are as defined above, and $R^6$ represents a hydrogen atom or a protecting group.

Reaction Scheme F uses as starting materials an alcohol compound of formula (7), wherein $R^1$, $R^2$, $R^3$, W and Y' are as defined above which may be prepared by the procedure described in, for example, J. Am. Chem. Soc., 64, 440 (1942), J. Am. Chem. Soc., 94, 227 (1972), J. Chem. Soc. Perkin Trans. I, 1591 (1983), Japanese Patent Kokai Application No. Sho 58-83698 (=Japanese Patent Publication No. Hei 1-33114), Japanese Patent Kokai Application No. Sho 58-174342 (=Japanese Patent Publication No. Hei 1-39411) or J. Takeda Res. Lab., 45, No. 3 & 4, 73 (1986), followed by conversion by conventional means, and a thiazolidine compound of formula (8) which is unsubstituted or which is substituted by a protecting group. The compounds of formula (7) and (8) are subjected to a dehydration reaction, for example the Mitsunobu reaction (Fieser & Fieser, "Reagents for Organic Synthesis", Vol. 6, pp 645, A Wiley-Interscience Publication, edited by John Wiley & Sons), to give the desired compound of formula (9).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene or toluene; aliphatic hydrocarbons, such as hexane or heptane; ethers, such as tetrahydrofuran or dioxane; halogenated hydrocarbons, especially halogenated aliphatic hydrocarbons, such as methylene chloride; and sulfoxides, such as dimethyl sulfoxide. The molar ratio of the compound of formula (7) to the compound of formula (8) is not particularly critical but it is preferred to use from 1 to 3 moles of the compound of formula (8) per mole of the compound of formula (7).

The reaction can take place over a wide range of temperatures, and the precise reaction temperature is not critical to the invention, although the preferred temperature may vary, depending upon the nature of the starting materials and the solvent used. In general, we find it convenient to carry out the reaction at a temperature of from −20° to 150° C. The time required for the reaction may also vary widely, depending on many factors, notably the reaction temperature and the nature of the reagents and solvent employed. However, provided that the reaction is effected under the preferred conditions outlined above, a period of from 10 minutes to several tens of hours will usually suffice.

Where the compound of formula (9) thus obtained has a protecting group, for example, a trityl group, deprotectionmay, if desired, be achieved by treatment with an organic acid, such as trifluoroacetic acid, to produce an intermediate of formula (2). The deprotection reaction may be carried out in the presence or absence of a solvent. Where the reaction is carried out in the presence of a solvent, examples of solvents which my be used include: ethers, such as tetrahydrofuran or dioxane; and methylene chloride. The molar ratio of the trifluoroacetic acid to the intermediate of formula (9) is preferably from 0.5:1 to a large excess of the trifluoroacetic acid.

The reaction can take place over a wide range of temperatures, and the precise reaction temperature is not critical to the invention, although the preferred temperature may vary, depending upon the nature of the starting materials and the solvent used. In general, we find it convenient to carry out the reaction at a temperature of from −20° to 40° C. The time required for the reaction may also vary widely, depending on many factors, notably the reaction temperature and the nature of the reagents and solvent employed. However, provided that the reaction is effected under the preferred conditions outlined above, a period of from several minutes to several tens of hours will usually suffice.

Reaction Scheme G

In this method, an intermediate of formula (9) is prepared by converting a compound of formula (7) (see Reaction Scheme F) to an active ester derivative or a halogenated compound and then reacting the product with a compound of formula (8).

The compound of formula (7) may be converted to an active ester derivative, such as a methanesulfonate, benzenesulfonate or toluenesulfonate, by conventional means, or to a halogenated compound, such as a chloride, bromide or iodide, also by conventional means. The desired compound of formula (9) can then be prepared by reacting the active ester compound or the halogenated compound thus obtained with a compound of formula (8), which formula is shown in Reaction Scheme F.

The reaction of the active ester compound or the halogenated compound with the compound of formula (8) is normally carried out in the presence of a base, for example, an inorganic base, such as an alkali metal carbonate (for example, sodium carbonate or potassium carbonate), or an alkali metal hydroxide (for example, sodium hydroxide or potassium hydroxide); or an alkali metal alcoholate, such as sodium methoxide, sodium ethoxide or potassium t-butoxide, or a metal hydride, such as sodium hydride, potassium hydride or lithium hydride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. The preferred solvent used may vary depending upon the nature of the base used. Examples of suitable solvents include: aromatic hydrocarbons, such as benzene, toluene or xylene; ethers, such as diethyl ether, tetrahydrofuran or dioxane; amides, such as dimethylformamide or dimethylacetamide; and organic sulfur compounds, such as dimethyl sulfoxide or sulfolane. Of these, we prefer the amides. The molar ratio of the compound of formula (8) to the base is normally from 0.5:1 to 5:1, more preferably from 1:1 to 3:1. The molar ratio of the compound of formula (8) to the active ester compound or the halogenated compound is normally from 0.5:1 to 4:1, more preferably from 1:1 to 3:1.

The reaction can take place over a wide range of temperatures, and the precise reaction temperature is not critical to the invention. In general, we find it convenient to carry out the reaction at a temperature of from 0° to 50° C., more preferably 5° to 20° C. The time required for the reaction may also vary widely, depending on many factors, notably the reaction temperature and the nature of the reagents and solvent employed. However, provided that the reaction is effected under the preferred conditions outlined above, a period of from several minutes to several tens of hours will usually suffice. The protecting group can, if desired, then be eliminated by the procedure described in Reaction Scheme F.

Reaction Scheme H

In this method, an intermediate of formula (2) can be prepared by the procedure described in, for example, European Patent Publication No. 306 228 (=Japanese Patent Kokai Application No. Hei 1-131169).

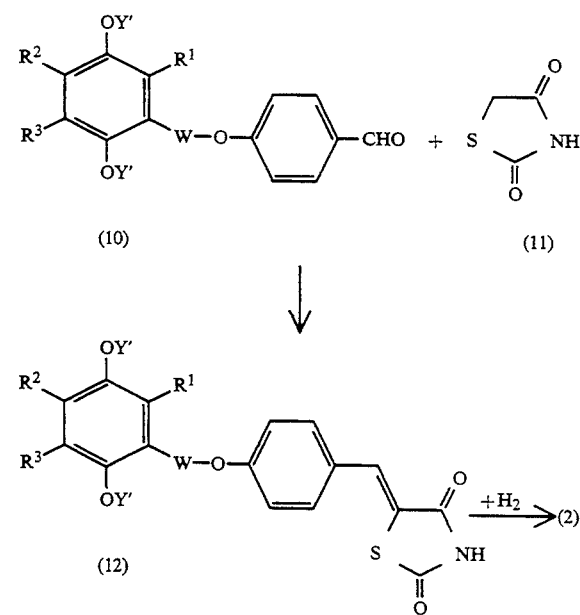

In the above formula, $R^1$, $R^2$, $R^3$, $Y'$ and $W$ are as defined above.

In this reaction scheme, the intermediate of formula (2) can be prepared by a condensation reaction between an aldehyde compound of formula (10), prepared by the procedure described in the Patent cited above, with thiazolidine-2,4-dione of formula (11) to produce a compound of formula (12), followed by reducing the product.

After completion of any of the above reactions, the desired compounds can be recovered from the reaction mixture and, if necessary, purified by conventional means, for example by the various chromatography techniques, such as column chromatography, or by recrystallization, reprecipitation or the like. An example of such a recovery procedure comprises: adding a solvent to the reaction mixture and then distilling off the solvent from the extract. The residue thus obtained can be purified by column chromatography through silica gel or the like to give the desired compound in a pure state.

Moreover, where the compound obtained comprises a mixture of various isomers, these isomers can be separated by conventional separating means in an appropriate stage.

BIOLOGICAL ACTIVITY

The thiazolidine compounds of the present invention showed excellent hypoglycemic activity and an outstanding inhibitory action against hepatic gluconeogenesis in a test system using genetically diabetic animals. Accordingly, it is expected that the compounds of the invention will be useful for the treatment and/or prevention of diabetes, diabetic complications, hyperlipidemia, hyperlipoperoxidemia, obesity-related hypertension, osteoporosis and the like.

The compounds of the present invention can be administered in various forms, depending on the disorder to be treated and the condition of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as a vehicle, a binder, a disintegrator, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, for the treatment of diabetes, diabetic complications and/or hyperlipemia, a daily dosage of from 1 to 1000 mg of the compound is recommended for an adult human patient, and this may be administered in a single dose or in divided doses.

The activity of the compounds of the present invention is illustrated by the following Experiment.

Experiment

Hypoglycemic activity

The test animals used were diabetic male mice of the KK strain, each having a body weight more than 40 g. Each animal was orally administered 50 mg/kg of a test compound and then allowed to feed freely for 18 hours. At the end of this time, blood was collected from the tail veins without anesthesia. The blood glucose level (BGL) was determined by means of a glucose analyzer (GL-101, manufactured by Mitsubishi Kasei Co.).

The blood glucose lowering rate was calculated by the following equation:

Blood glucose lowering rate (%) =

$$[(BGL_s - BGL_t)/BGL_s] \times 100$$

where:

$BGL_s$ is the BGL in the group administered a solvent; and $BGL_t$ is the BGL in the group administered a test compound.

The results are shown in the following Table, in which each compound of the present invention is identified by the number of one of the following Examples in which its preparation is illustrated.

As a control, we also used as the test compound 5-{4-[2-Methyl-2-hydroxy-4-(3,5,6-trimethyl-1,4-benzoquinon-2-yl)butoxy]benzyl}thiaz olidin-2,4-dione, which is the compound of Example 1 described in European Patent Publication No. 441 605). This is identified as "Control".

TABLE

| Compound | BGL lowering rate (%) |
| --- | --- |
| Compound of Example 2 | 28.8 |
| Compound of Example 5 | 30.4 |
| Compound of Example 6 | 30.5 |
| Compound of Example 8 | 19.7 |
| Compound of Example 9 | 22.1 |
| Control | −0.5 |

As can be seen from the results shown in the Table, the compounds of the present invention showed a much greater activity than did the compound of the prior art.

The preparation of the compounds of the present invention is further illustrated by the following non-limiting Examples, and the preparation of various intermediates used in these Examples is illustrated in the subsequent Preparations. Certain of the Examples refer to the Reaction Schemes shown above; thus, in the Examples, "Method A-1" refers to the method of Reaction Scheme A, Step 1, "Method D" refers to the method of Reaction Scheme D, and so on.

EXAMPLE 1—(Method A- 1)

5-[4-(3,5,6-Trimethyl-1,4-benzoquinon-2-yloxy)benzyl]-thiazolidine-2,4-dione (Compound No. 1-1)

A solution of 2.1 g of ceric ammonium nitrate in a mixture of 2 ml of water and 2 ml of acetonitrile was added dropwise at 0° C. to a solution of 0.4 g of 5-[4-(2,4,5-trimethyl-3,6-dimethoxyphenoxy)benzyl]thiazolidine-2,4-dione (prepared as described in Preparation 2) in 3 ml of acetonitrile, and the resulting mixture was stirred at the same temperature for 1 hour. At the end of this time, the reaction mixture was poured into water, after which it was extracted with ethyl acetate. The extract was washed with a saturated aqueous solution of sodium chloride and then dried over anhydrous sodium sulfate. The solvent was then removed from the extract by distillation under reduced pressure, and the residue thus obtained was purified by column chromatography through silica gel, using a 4:1 by volume mixture of benzene and ethyl acetate as the eluent, to give 260 mg of the title compound, melting at 153°–156° C. (with decomposition).

EXAMPLE 2—(Method D)

5-{4-[3-(3,5,6-Trimethyl-1,4-benzoquinon-2-yl)propoxy]benzyl}thiazolidine-2,4-dione sodium salt (Compound No. 1-8)

39 mg of sodium 2-ethylhexanoate were added to a solution of 97 mg of 5-{4-[3-(3,5,6-trimethyl-1,4-benzoquinon-2-yl)propoxy]benzyl}thiazolid ine-2,4-dione (prepared as described in Example 8) in 4 ml of ethyl acetate, and the resulting mixture Was stirred at room temperature for 18 hours. At the end of this time, the solvent was removed by distillation under reduced pressure from the reaction mixture, and the residue thus obtained was crystallized from hexane, to give 98 mg of the title compound as yellow crystals, melting at 238°–242° C. (with decomposition).

EXAMPLES 3 to 16

Following procedures similar to those described in Examples 1 and 2 above, we also prepared compounds of formula (I-4):

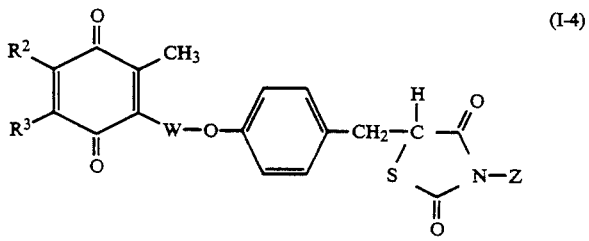

in which $R^2$, $R^3$, W and Z are as defined in Table 4. In the Table, the column "As in Ex. No." shows the number of the Example whose procedure was followed.

In this and subsequent Tables, the following abbreviations were used:

| | |
|---|---|
| Ac = | acetyl |
| Me = | methyl; |
| MeO = | methoxy; |
| m.p. = | melting point |

(d) is a decomposition point;
(s) is a softening point; and
Under the column "W", "-" means a single bond.

TABLE 4

| Ex. No. | Cpd. No. | As in Ex. No. | $R^2$ | $R^3$ | W | Z | Property, m.p. (°C.) |
|---|---|---|---|---|---|---|---|
| 3 | 1-2 | 2 | Me | Me | — | Na | 280–290 (d) |
| 4 | 1-3 | 1 | Me | Me | —CH$_2$— | H | 179–181 (d) |
| 5 | 1-4 | 2 | Me | Me | —CH$_2$— | Na | 190–193 (d) |
| 6 | 1-5 | 1 | Me | Me | —(CH$_2$)$_2$— | H | 157–158 |
| 7 | 1-6 | 2 | Me | Me | —(CH$_2$)$_2$— | Na | ca. 210 (d) |
| 8 | 1-7 | 1 | Me | Me | —(CH$_2$)$_3$— | H | 118–120 (d) |
| 9 | 1-9 | 1 | Me | Me | —(CH$_2$)$_4$— | H | foamy yellow powder* |
| 10 | 1-10 | 2 | Me | Me | —(CH$_2$)$_4$— | Na | 219–221 (d) |
| 11 | 1-15 | 1 | MeO | MeO | —CH$_2$— | H | foamy yellow powder* |
| 12 | 1-16 | 2 | MeO | MeO | —CH$_2$— | Na | 70–72 (s) |
| 13 | 1-19 | 1 | MeO | MeO | —(CH$_2$)$_3$— | H | 60–70 (s) |
| 14 | 1-20 | 2 | MeO | MeO | —(CH$_2$)$_3$— | Na | ca. 195 (d) |
| 15 | 1-21 | 1 | MeO | MeO | —(CH$_2$)$_4$— | H | red glass* |
| 16 | 1-22 | 2 | MeO | MeO | —(CH$_2$)$_4$— | Na | 198–201 (d) |

TABLE 4-continued

*Nuclear Magnetic Resonance spectrum of the compound of Example 9 (δ ppm, CDCl$_3$):
1.63 (2H, multiplet);
1.83 (2H, multiplet);
2.01 (6H, singlet);
2.03 (3H, singlet);
2.55 (2H, triplet, J = 7 Hz);
3.10 (1H, doublet of doublets, J = 14 & 9 Hz);
3.45 (1H, doublet of doublets, J = 14 & 4 Hz);
3.96 (2H, triplet, J = 6 Hz);
4.50 (1H, doublet of doublets, J = 9 & 4 Hz);
6.83 (2H, doublet, J = 9 Hz);
7.13 (2H, doublet, J = 9 Hz);
8.24 (1H, broad singlet).
*Nuclear Magnetic Resonance spectrum of the compound of Example 11 (δ ppm, CDCl$_3$):
2.16 (3H, singlet);
3.15 (1H, doublet of doublets, J = 14 & 9 Hz);
3.45 (1H, doublet of doublets, J = 14 & 4 Hz);
4.02 (3H, singlet);
4.07 (3H, singlet);
4.51 (1H, doublet of doublets, J = 9 & 4 Hz);
4.93 (2H, singlet);
6.90 (2H, doublet, J = 7 Hz);
7.16 (2H, doublet, J = 7 Hz);
8.27 (1H, broad singlet).
*Nuclear Magnetic Resonance spectrum of the compound of Example 15 (δ ppm, CDCl$_3$):
1.5–1.9 (6H, multiplet);
2.03 (3H, singlet);
2.54 (2H, triplet, J = 8 Hz);
3.11 (1H, doublet of doublets, J = 14 & 9 Hz);
3.44 (1H, doublet of doublets, J = 14 & 4 Hz);
3.98 (3H, singlet);
3.99 (3H, singlet);
4.50 (1H, doublet of doublets, J = 9 & 4 Hz);
6.83 (2H, doublet, J = 9 Hz);
7.13 (2H, doublet, J = 9 Hz);
7.97 (1H, broad singlet).

EXAMPLES 17 to 22

Following procedures similar to those described in Examples 1 and 2 above, we also prepared compounds of formula (I-5):

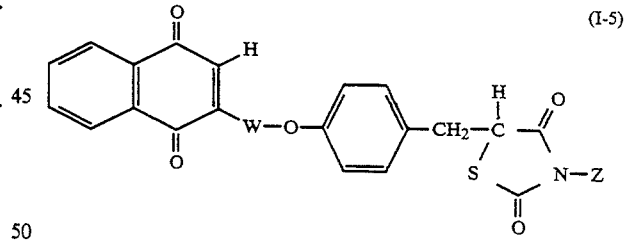

in which W and Z are as defined in Table 5. In the Table, the column "As in Ex. No." shows the number of the Example whose procedure was followed. The abbreviations used are as given above for Table 4.

TABLE 5

| Ex. No. | Cpd. No. | As in Ex. No. | W | Z | Property, m.p. (°C.) |
|---|---|---|---|---|---|
| 17 | 2-5 | 1 | —(CH$_2$)$_2$— | H | pale yellow powder, 163–166 |
| 18 | 2-6 | 2 | —(CH$_2$)$_2$— | Na | brown powder >200 (d) |
| 19 | 2-7 | 1 | —(CH$_2$)$_3$— | H | pale yellow powder*, 76–82 (s) |
| 20 | 2-8 | 2 | —(CH$_2$)$_3$— | Na | pale yellow powder* 236–239 (d) |
| 21 | 2-9 | 1 | —(CH$_2$)$_4$— | H | yellow powder 145–147 |
| 22 | 2-10 | 2 | —(CH$_2$)$_4$— | Na | yellow powder |

TABLE 5-continued 234-236 (d)

*Nuclear Magnetic Resonance spectrum of the compound of Example 19 (δ ppm, CDCl₃):
2.03–2.16 (2H, multiplet);
2.78 (2H, triplet, J = 8 Hz);
3.12 (1H, doublet of doublets, J = 15 & 9 Hz);
3.42 (1H, doublet of doublets, J = 15 & 4 Hz);
4.03 (2H, triplet, J = 6 Hz);
4.50 (1H, doublet of doublets, J = 9 & 4 Hz);
6.78 (2H, doublet, J = 9 Hz);
6.80 (1H, singlet);
7.12 (2H, doublet, J = 9 Hz);
7.71–7.77 (2H, multiplet);
8.02–8.13 (2H, multiplet);
8.20 (1H, broad singlet).

*Nuclear Magnetic Resonance spectrum of the compound of Example 20 (δ ppm, CDCl₃):
1.96–2.04 (2H, multiplet);
2.58–2.76 (2H, multiplet);
2.62 (1H, doublet of doublets, J = 14 & 10 Hz);
3.30 (1H, doublet of doublets, J = 14 & 3 Hz);
4.00 (2H, triplet, J = 6 Hz);
4.12 (1H, doublet of doublets, J = 10 & 3 Hz);
6.75 (2H, doublet, J = 8 Hz);
6.94 (1H, singlet);
7.07 (2H, doublet, J = 8 Hz);
7.81–8.04 (4H, multiplet).

EXAMPLE 23—(Method E)

5-[4-(3-Chloro-1,4-naphthoquinon-2-yloxy)benzyl]-thiazolidine-2,4-dione (Compound No. 2-20)

A mixture of 5.8 g of butyl 2-bromo-3-[4-(1,4-diacetoxy-3-chloro-2-naphthyloxy)phenyl]propiona te (prepared as described in Preparation 18), 1 g of thiourea and 10 ml of sulfolane was heated at 120° C. for 5 hours under an atmosphere of nitrogen. At the end of this time, 20 ml of ethylene glycol monomethyl ether and 10 ml of 2N aqueous hydrochloric acid were added to the mixture in the presence of atmospheric oxygen, and the resulting mixture was heated at 100° C. for 6 hours. The reaction mixture was then poured into water, after which it was extracted with benzene. The extract was washed with water and dried over anhydrous magnesium sulfate. The solvent was then removed from the extract by distillation under reduced pressure, and the resulting residue was purified by column chromatography through silica gel, using a 4:1 by volume mixture of benzene and ethyl acetate as the eluent. About 2.4 g of the title compound were obtained by recrystallization from a mixture of tetrahydrofuran and hexane as crystals, melting at 250°–252° C.

Nuclear Magnetic Resonance Spectrum (hexadeuterated dimethyl sulfoxide) δ ppm:
3.09 (1H, doublet of doublets, J=14 & 9 Hz);
3.37 (1H, doublet of doublets, J=14 & 4 Hz);
4.91 (1H, doublet of doublets, J=9 & 4 Hz);
7.13 (2H, doublet, J=8 Hz);
7.22 (2H, doublet, J=8 Hz);
7.85–7.96 (2H, multiplet);
7.96–8.01 (1H, multiplet);
8.11 (1H, doublet, J=7 Hz);
12.04 (1H, broad singlet, disappeared on adding deuterium oxide).

EXAMPLE 24—(Method B)

5-{4-[3-(3,5,6-Trimethyl-1,4-benzoquinon-2-yl)propoxy]benzylidene}thiazolidine-2,4-dion e (Compound No. 3-3)

Following a procedure similar to that described in Example 1, but using 15.8 g of 5-{4-[3-(2,5-dimethoxy-3,4,6-trimethylphenyl)propoxy]benzyl}thiazolidine-2,4-dione (prepared as described in Preparation 4), 78.1 g of ceric ammonium nitrate and 350 ml of acetonitrile, 1.7 g of the title compound, melting at 230°–232° C., were obtained.

Nuclear Magnetic Resonance Spectrum (hexadeuterated dimethyl sulfoxide) δ ppm:
1.80–1.87 (2H, multiplet);
1.92 (3H, singlet);
1.94 (6H, singlet);
2.60 (2H, triplet, J=7 Hz);
4.04 (2H, triplet, J=6 Hz);
7.04 (2H, doublet, J=9 Hz);
7.53 (2H, doublet, J=9 Hz);
7.77 (1H, singlet);
12.49 (1H, broad singlet).

EXAMPLE 25—(Method D)

5-{4-[3-(3,5,6-Trimethyl-1,4-benzoquinon-2-yl)propoxy]benzylidene}thiazoline-2,4-dione sodium salt (Compound No. 1-8)

27 mg of sodium methoxide were added to a solution of 200 mg of 5-{4-[3-(3,5,6-trimethyl-1,4-benzoquinon-2-yl)propoxy]benzylidene}thiazolidine -2,4-dione (prepared as described in Example 24) dissolved in 300 ml of methanol, whilst heating, and then the solvent was removed from the reaction mixture by distillation under reduced pressure. The crystals thus obtained were washed with hexane, to give 190 mg of the title compound, melting at 260°–265° C. (with decomposition).

Nuclear Magnetic Resonance Spectrum (hexadeuterated dimethyl sulfoxide) δ ppm:
1.78–1.88 (2H, multiplet);
1.92 (3H, singlet);
1.94 (3H, singlet);
1.95 (3H, singlet);
2.60 (2H, triplet, J=7 Hz);
3.99 (2H, triplet, J=6 Hz);
6.94 (2H, doublet, J=9 Hz);
7.26 (1H, singlet);
7.44 (2H, doublet, J=9 Hz).

PREPARATION 1 (Method E)

Butyl 2-bromo-3-[4-(2,4,5-trimethyl-3,6-dimethoxyphenoxy)-phenyl]propionate

1(a) 2,5-Dimethoxy-3,4,6-trimethylphenol

A solution of 9.4 g of m-chloroperbenzoic acid (70% purity) in 100 ml of methylene chloride was added dropwise, whilst ice-cooling, to a solution of 4.6 g of 1,4-dimethoxy-2,3,5-trimethylbenzene in 20 ml of methylene chloride, and the resulting mixture was stirred at the same temperature for 30 minutes and then at room temperature for 5 hours. At the end of this time, the reaction mixture was washed with a 5% w/v aqueous solution of sodium hydrogensulfite, with a 5% w/v aqueous solution of sodium hydrogencarbonate and with water, in that order, after which it was dried over anhydrous sodium sulfate. The solvent was then removed from the reaction mixture by distillation under reduced pressure, and the resulting residue was purified by column chromatography through silica gel, using benzene and a 50:1 by volume mixture of benzene and ethyl acetate as the eluents, to give 1.3 g of the title compound.

Nuclear Magnetic Resonance Spectrum (CDCl$_3$) δ ppm:
- 2.12 (3H, singlet);
- 2.17 (6H, singlet);
- 3.65 (3H, singlet);
- 3.73 (3H, singlet);
- 5.59 (1H, singlet, disappeared on adding deuterium oxide).

1(b) 2,5-Dimethoxy-3,4,6-trimethyl-1-(4-nitrophenoxy)benzene 5.8 g of 2,5-dimethoxy-3,4,6-trimethylphenol [prepared as described in step (a) above] in 10 ml of dimethylformamide were added to a suspension of 1.4 g of sodium hydride (as a 55% w/w dispersion in mineral oil) in 50 ml of dimethylformamide, whilst ice-cooling, and the mixture was stirred at room temperature for 2 hours. At the end of this time, a solution of 4.6 g of p-fluoronitrobenzene in 10 ml of dimethylformamide was added to the mixture, whilst ice-cooling. The mixture was then stirred at room temperature for 1 hour, and then at 80° C. for 7 hours. At the end of this time, the mixture was poured into water, and the resulting crude oil was extracted with benzene. The benzene extract was washed with water and dried over anhydrous sodium sulfate. The solvent was then removed by distillation under reduced pressure, and the resulting oil was purified by column chromatography through silica gel, using a 4:1 by volume mixture of benzene and hexane, followed by benzene alone, as the eluent, to give 3.9 g of the title compound.

Nuclear Magnetic Resonance Spectrum (CDCl$_3$) δ ppm:
- 2.08 (3H, singlet);
- 2.19 (3H, singlet);
- 2.23 (3H, singlet);
- 3.65 (3H, singlet);
- 3.70 (3H, singlet);
- 6.89 (2H, doublet, J=9 Hz);
- 8.17 (2H, doublet, J=9 Hz).

1(c) 4-(2,5-Dimethoxy-3,4,6-trimethylphenoxy)aniline

A mixture of 4.8 g of 2,5-dimethoxy-3,4,6-trimethyl-1-(4-nitrophenoxy)benzene [prepared as described in step (b) above], 1.0 g of 10% w/w palladium-on-charcoal and 100 ml of ethanol was stirred under a hydrogen atmosphere at room temperature for 3 hours. At the end of this time, the catalyst was filtered off, and the filtrate was concentrated by evaporation under reduced pressure, to give 3.9 g of the title compound. p Nuclear Magnetic Resonance Spectrum (CDCl$_3$) δ ppm:
- 2.09 (3H, singlet);
- 2.17 (3H, singlet);
- 2.20 (3H, singlet);
- 3.4 (2H, broad singlet, disappeared on adding deutrium oxide);
- 3.667 (3H, singlet);
- 3.674 (3H, singlet);
- 6.59 (2H, doublet, J=9 Hz);
- 6.65 (2H, doublet, J=9 Hz).

1(d) Butyl 2-bromo-3-[4-(2,4,5-trimethyl-3,6-dimethoxyphenoxy)phenyl]propionate 7.7 g of a 47% w/v aqueous solution of hydrobromic acid and a solution of 1.3 g of sodium nitrite in 3 ml of water were added dropwise, in that order, to a solution of 4.3 g of 4-(2,5-dimethoxy-3,4,6-trimethylphenoxy)aniline [prepared as described in step (c) above] in 10 ml of acetone, after which 21 ml of butyl acrylate were added to the mixture. After that, 0.3 g of cupric bromide was gradually added and the resulting mixture was stirred at room temperature for 4 hours. At the end of this time, the reaction mixture was poured into water, after which it was extracted with benzene. The extract was washed with water and dried over anhydrous sodium sulfate. The solvent was removed by distillation under reduced pressure from the extract, and the residue thus obtained was purified by column chromatography through silica gel, using a 3:7 by volume mixture of hexane and benzene as the eluent, to give 5.7 g of the title compound.

Nuclear Magnetic Resonance Spectrum (CDCl$_3$) δ ppm:
- 0.87 (3H, singlet);
- 0.91 (3H, singlet);
- 0.93 (3H, singlet);
- 1.2–1.4 (2H, multiplet);
- 1.5–1.65 (2H, multiplet);
- 2.07 (3H, singlet);
- 2.17 (3H, singlet);
- 2.21 (3H, singlet);
- 3.16 (1H, doublet of doublets, J=7 & 10 Hz);
- 3.39 (1H, doublet of doublets, J=9 & 14 Hz);
- 3.65 (3H, singlet);
- 3.68 (3H, singlet);
- 4.11 (2H, triplet, J=7 Hz);
- 4.33 (1H, doublet of doublets, J=7 & 9 Hz);
- 6.73 (2H, doublet, J=9 Hz);
- 7.08 (2H, doublet, J=9 Hz).

PREPARATION 2—(Method E)

5-[4-(2,4,5-Trimethyl-3,6-dimethoxyphenoxy)benzyl]-thiazolidine-2,4-dione

A mixture of 5.7 g of butyl 2-bromo-3-[4-(2,4,5-trimethyl-3,6-dimethoxyphenoxy)phenyl]propionate (prepared as described in Preparation 1), 1.2 g of thiourea and 10 ml of sulfolane was heated at 120° C. for 5 hours under an atmosphere of nitrogen, and then 20 ml of ethylene glycol monomethyl ether and 10 ml of 2N aqueous hydrochloric acid were added to the resulting mixture. The mixture was then heated at 100° C. for 5 hours, after which the reaction mixture was poured into water and then extracted with benzene. The extract was washed with water and dried over anhydrous sodium sulfate. The solvent was removed from the extract by distillation under reduced pressure, and the residue thus obtained was purified by column chromatography through silica gel, using a 9:1 by volume mixture of benzene and ethyl acetate as the eluent, to give 4.7 g of the title compound as a white glassy powder softening at 47°–50° C.

Nuclear Magnetic Resonance Spectrum (hexadeuterated dimethyl sulfoxide) δ ppm:
- 1.97 (3H, singlet);
- 2.11 (3H, singlet);
- 2.15 (3H, singlet);

3.04 (1H, doublet of doublets, J=9 & 14 Hz);
3.32 (1H, doublet of doublets, J=4 & 14 Hz);
3.54 (3H, singlet);
3.61 (3H, singlet);
4.85 (1H, doublet of doublets, J=4 & 9 Hz);
6.70 (2H, doublet, J=8 Hz);
7.15 (2H, doublet, J=8 Hz).

PREPARATION 3—(Method F)

5-{4-[2-(2,4,5-Trimethyl-3,6,-dimethoxyphenyl)ethoxy]benzyl}thiazolidine-2,4-dione 3.2 g of diethyl azodicarboxylate were added dropwise, whilst ice-cooling and under an atmosphere of nitrogen, to a solution of 3.5 g of 2-(2,4,5-trimethyl-3,6-dimethoxypenyl)ethanol, 7.3 g of 5-(4-hydroxybenzyl)-3-triphenylmethylthiazolidine-2,4-dione (prepared as described in Preparation 32) and 4.9 g of triphenylphosphine in 100 ml of tetrahydrofuran, and the resulting mixture was stirred at room temperature for 5 hours. At the end of this time, the reaction mixture was poured into water, after which it was extracted with ethyl acetate. The extract was washed with a saturated aqueous solution of sodium chloride and dried over anhydrous sodium sulfate. The solvent was then removed from the extract by distillation under reduced pressure, and the resulting residue was purified by column chromatography through silica gel, using a 4:1 by volume mixture of hexane and ethyl acetate as the eluent, to give 5-{4-[2-(2,4,5-trimethyl-3,6-dimethoxyphenyl)ethoxy]benzyl}-3-triphenylmethylthia zolidine-2,4-dione as an oily intermediate. 50 ml of trifluoroacetic acid were added, whilst ice-cooling, to 7.9 g of the intermediate, and the resulting mixture was stirred for 1 hour. At the end of this time, the reaction mixture was diluted with water, after which it was extracted with ethyl acetate. The extract was washed twice, each time with a saturated aqueous solution of sodium hydrogencarbonate; it was then dried over anhydrous sodium sulfate. The solvent was then removed by distillation under reduced pressure, and the residue thus obtained was purified by column chromatography through silica gel, using a 3:1 by volume mixture of hexane and ethyl acetate as the eluent, to give 3.6 g of the title compound softening at 44°–45° C.

PREPARATION 4—(Method G)

5-{4-[3-(2,5-Dimethoxy-3,4,6-trimethylphenyl)propoxy]benzyl}thiazolidine-2,4-dione 8.01 g of 5-(4-hydroxybenzyl)thiazolidine-2,4-dione were added in small amounts, whilst ice-cooling, to a suspension prepared by adding 80 ml of dimethylformamide to 3.45 g of sodium hydride (as a 55% w/w dispersion in mineral oil, and which had previously been washed twice with dry hexane). The resulting mixture was stirred at the same temperature for 30 minutes, after which a solution of 13.73 g of 3-(2,5-dimethoxy-3,4,6-trimethylphenyl)propyl iodide (prepared as described in Preparation 24), in 20 ml of dimethylformamide was added dropwise to the solution. The mixture was then stirred at room temperature for 1.5 hours. At the end of this time, the reaction mixture was poured into 300 ml of ice-water, after which it was extracted with ethyl acetate. The extract was washed twice, each time with a saturated aqueous solution of sodium chloride, and dried over anhydrous sodium sulfate. The solvent was then removed from the extract by distillation under reduced pressure, and the residue thus obtained was purified by column chromatography through silica gel, using a gradient elution method with mixtures of hexane and ethyl acetate ranging from 3:1 to 2:1 by volume as the eluent, to give 6.7 g of the title compound, melting at 111°–113° C.

PREPARATIONS 5 TO 13

Following procedures similar to those described in Preparations 3 and 4 above and 18 (given hereafter), we also prepared compounds of formula (I-6):

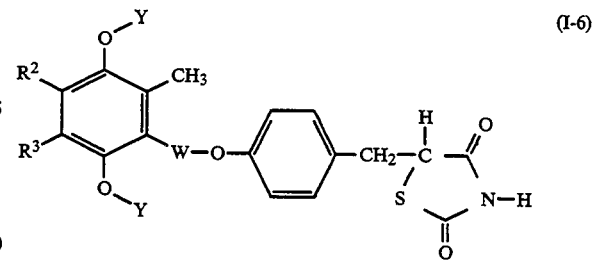

in which $R^2$, $R^3$, W and Y are as defined in Table 6. The abbreviations used are as given above for Table 4. In the Table, the column "As in Prep." shows the number of the Preparation whose procedure was followed.

TABLE 6

| Prep. No. | $R^2$ | $R^3$ | Y | W | As in Prep. | Property, m.p. (°C.) |
|---|---|---|---|---|---|---|
| 5 | Me | Me | Me | —$CH_2$— | 4 | 178–180* |
| 6 | Me | Me | Me | —$(CH_2)_4$— | 4 | 89–91 |
| 7 | MeO | MeO | Me | —$CH_2$— | 4 | white glass* |
| 8 | MeO | MeO | Me | —$(CH_2)_2$— | 3 | white foam* |
| 9 | MeO | MeO | Me | —$(CH_2)_3$— | 4 | pale yellow oil* |
| 10 | MeO | MeO | Me | —$(CH_2)_4$— | 4 | colorless oil* |
| 11 | Me | Me | Ac | —$(CH_2)_2$— | 18 | 122–125 |
| 12 | Me | Me | Ac | —$(CH_2)_3$— | 18 | white foam* |
| 13 | Me | Me | Ac | —$(CH_2)_4$— | 18 | white foam* |

*Nuclear Magnetic Resonance spectrum of the compound of Preparation 5 (δ ppm, CDCl$_3$):
2.20 (3H, singlet);
2.22 (3H, singlet);
2.29 (3H, singlet);
3.12 (1H, doublet of doublets, J = 9 & 14 Hz);
3.48 (1H, doublet of doublets, J = 4 & 14 Hz);
3.68 (3H, singlet);
3.69 (3H, singlet);
4.52 (1H, doublet of doublets, J = 4 & 9 Hz);
5.05 (2H, singlet);
6.98 (2H, doublet, J = 9 Hz);
7.17 (2H, doublet, J = 9 Hz);
8.14 (1H, broad singlet).

*Nuclear Magnetic Resonance spectrum of the compound of Preparation 7 (δ ppm, CDCl$_3$):
2.25 (3H, singlet);
3.13 (1H, doublet of doublets, J = 14 & 9 Hz);
3.48 (1H, doublet of doublets, J = 14 & 4 Hz);
3.81 (3H, singlet);
3.83 (1H, singlet);
3.92 (3H, singlet);
3.94 (3H, singlet);
4.52 (1H, doublet of doublets, J = 9 & 4 Hz);
5.01 (2H, singlet);
6.98 (2H, doublet, J = 9 Hz);
7.18 (2H, doublet, J = 9 Hz);
8.07 (1H, broad singlet).

*Nuclear Magnetic Resonance spectrum of the compound of Preparation 8 (δ ppm, CDCl$_3$):
2.23 (3H, singlet);
3.0–3.2 (3H, multiplet);
3.44 (1H, doublet of doublets, J = 14 & 4 Hz);
3.79 (3H, singlet);
3.87 (3H, singlet);
3.91 (3H, singlet);

TABLE 6-continued 3.92 (3H, singlet);
4.03 (2H, triplet, J = 7 Hz);
4.50 (1H, doublet of doublets, J = 9 & 4 Hz);
6.87 (2H, doublet, J = 8 Hz);
7.13 (2H, doublet, J = 8 Hz);
8.14 (1H, broad singlet).
*Nuclear Magnetic Resonance spectrum of the compound of Preparation 9 (δ ppm, CDCl$_3$):
1.85–2.05 (2H, multiplet);
2.17 (3H, singlet);
2.76 (2H, triplet, J = 8 Hz);
3.11 (1H, doublet of doublets, J = 14 & 9 Hz);
3.45 (1H, doublet of doublets, J = 14 & 4 Hz);
3.78 (3H, singlet);
3.82 (3H, singlet);
3.89 (3H, singlet);
3.91 (3H, singlet);
3.99 (2H, triplet, J = 7 Hz);
4.50 (1H, doublet of doublets, J = 9 & 4 Hz);
6.85 (2H, doublet, J = 9 Hz);
7.14 (2H, doublet, J = 9 Hz);
8.30 (1H, broad singlet).
*Nuclear Magnetic Resonance spectrum of the compound of Preparation 10 (δ ppm, CDCl$_3$):
1.63 (2H, multiplet);
1.84 (2H, multiplet);
2.17 (3H, singlet);
2.64 (2H, triplet, J = 6 Hz);
3.10 (1H, doublet of doublets, J = 14 & 9 Hz);
3.44 (1H, doublet of doublets, J = 14 & 4 Hz);
3.78 (3H, singlet);
3.81 (3H, singlet);
3.89 (3H, singlet);
3.90 (3H, singlet);
3.98 (2H, striplet, J = 6 Hz);
4.50 (1H, doublet of doublets, J = 9 & 4 Hz);
6.84 (2H, doublet, J = 9 Hz);
7.13 (2H, doublet, J = 9 Hz);
7.92 (1H, broad singlet).
*Nuclear Magnetic Resonance spectrum of the compound of Preparation 12 (δ ppm, CDCl$_3$):
1.92 (2H, triplet, J = 6 Hz);
2.03 (3H, singlet);
2.05 (3H, singlet);
2.07 (3H, singlet);
2.30 (3H, singlet);
2.34 (3H, singlet);
2.69 (2H, multiplet);
3.14 (1H, doublet of doublets, J = 14 & 9 Hz);
3.45 (1H, doublet of doublets, J = 14 & 4 Hz);
3.94 (2H, triplet, J = 6 Hz);
4.51 (1H, doublet of doublets, J = 9 & 4 Hz);
6.84 (2H, doublet, J = 9 Hz);
7.14 (2H, doublet, J = 9 Hz);
7.83 (1H, broad singlet).
*Nuclear Magnetic Resonance spectrum of the compound of Preparation 13 (δ ppm, CDCl$_3$):
1.61 (2H, multiplet);
1.83 (2H, multiplet);
2.03 (3H, singlet);
2.05 (3H, singlet);
2.08 (3H, singlet);
2.29 (3H, singlet);
2.35 (3H, singlet);
2.55 (2H, multiplet);
3.11 (1H, doublet of doublets, J = 14 & 9 Hz);
3.45 (1H, doublet of doublets, J = 14 & 4 Hz);
3.95 (2H, triplet, J = 6 Hz);
4.50 (1H, doublet of doublets, J = 9 & 4 Hz);
6.83 (2H, doublet, J = 9 Hz);
7.13 (2H, doublet, J = 9 Hz);
7.99 (1H, broad singlet).

PREPARATIONS 14 TO 16

Following procedures similar to those described in Preparations 3 and 4 above, we also prepared compounds of formula (I-7):

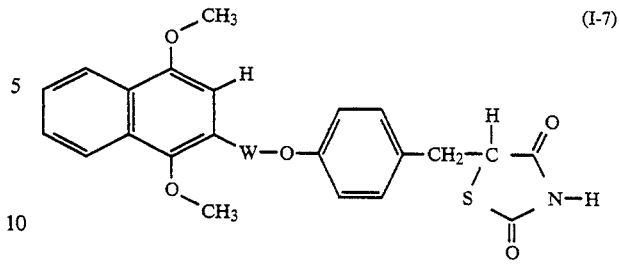

in which W is as defined in Table 7. The abbreviations used are as given above for Table 4.

TABLE 7

| Preparation No. | W | As in Prep. | Property and m.p. (°C.) |
|---|---|---|---|
| 14 | —(CH$_2$)$_2$— | 3 | pale yellow powder*, 60–65 (s) |
| 15 | —(CH$_2$)$_3$— | 4 | pale yellow powder*, 45–50 (s) |
| 16 | —(CH$_2$)$_4$— | 4 | pale yellow powder*, 37–42 (s) |

*Nuclear Magnetic Resonance spectrum of the compound of Preparation 14 (δ ppm, CDCl$_3$):
3.10 (1H, doublet of doublets, J = 14 & 9 Hz);
3.28 (2H, triplet, J = 7 Hz);
3.44 (1H, doublet of doublets, J = 14 & 4 Hz);
3.93 (3H, singlet);
3.98 (3H, singlet);
4.25 (2H, triplet, J = 7 Hz);
4.49 (1H, doublet of doublets, J = 9 & 4 Hz);
6.71 (1H, singlet);
6.88 (2H, doublet, J = 9 Hz);
7.13 (2H, doublet, J = 9 Hz);
7.42–7.58 (2H, multiplet);
7.99–8.12 (1H, broad singlet);
8.03 (1H, doublet, J = 8 Hz);
8.22 (1H, doublet, J = 8 Hz).
*Nuclear Magnetic Resonance spectrum of the compound of Preparation 15 (δ ppm, CDCl$_3$):
2.12–2.25 (2H, multiplet);
2.99 (2H, triplet, J = 8 Hz);
3.10 (1H, doublet of doublets, J = 14 & 9 Hz);
3.45 (1H, doublet of doublets, J = 14 & 4 Hz);
3.88 (3H, singlet);
3.90 (3H, singlet);
4.01 (2H, triplet, J = 6 Hz);
4.50 (1H, doublet of doublets, J = 9 & 4 Hz);
6.61 (1H, singlet);
6.86 (2H, doublet, J = 9 Hz);
7.14 (2H, doublet, J = 9 Hz);
7.40–7.57 (2H, multiplet);
7.98–8.12 (1H, broad singlet);
8.02 (1H, doublet, J = 9 Hz);
8.20 (1H, doublet, J = 9 Hz).
*Nuclear Magnetic Resonance spectrum of the compound of Preparation 16 (δ ppm, CDCl$_3$):
1.84–1.93 (4H, multiplet);
2.83–2.92 (2H, multiplet);
3.10 (1H, doublet of doublets, J = 14 & 9 Hz);
3.44 (1H, doublet of doublets, J = 14 & 4 Hz);
3.87 (3H, singlet);
3.97 (3H, singlet);
3.95–4.04 (2H, multiplet);
4.50 (1H, doublet of doublets, J = 9 & 4 Hz);
6.63 (1H, singlet);
6.84 (2H, doublet, J = 9 Hz);
7.12 (2H, doublet, J = 9 Hz);
7.41–7.55 (2H, multiplet);
7.88 (1H, broad singlet);
8.02 (1H, doublet, J = 9 Hz);
8.20 (1H, doublet, J = 9 Hz).

PREPARATION 17

3-Chloro-2-(4-nitrophenxy)-1,4-naphthoquinone 10 g of 2,3-dichloro-1,4-naphthoquinone were added to a solution of 7 g of the sodium salt of p-nitrophenol in 100 ml of dimethylformamide, and the resulting mixture was stirred at room temperature for 5 hours. At the end of this time, the reaction mixture was poured into water, after which it was extracted with benzene. The extract was washed with water and dried over anhydrous sodium sulfate. The solvent was then removed from the extract by distillation under reduced pressure, and the residue thus obtained was purified by column chromatography through silica gel, using a 1:4 by volume mixture of hexane and benzene as the eluent, to give 10 g of the title compound, melting at 179°–182° C.

PREPARATION 18

Butyl 2-bromo-3-[4-(1,4-diacetoxy-3-chloro-2-naphthyloxy)phenyl]propionate

18(a)
3-Chloro-1,4-dihydroxy-2-(4-nitrophenoxy)naphthalene 1 g of sodium borohydride was added, whilst ice-cooling, to a solution of 11 g of 3-chloro-2-(4-nitrophenoxy)-1,4-naphthoquinone (prepared as described in Preparation 17) in 150 ml of methanol, and the mixture was stirred, whilst ice-cooling, for 30 minutes. The mixture was then poured into a mixture of ice and 15 ml of 2N aqueous hydrochloric acid to give a precipitate, which was collected by filtration, washed with water and dried under reduced pressure in the presence of phosphorus pentoxide, to give 9 g of 3-chloro-1,4-dihydroxy-2-(4-nitrophenoxy)naphthalene.

18(b)
1,4-Diacetoxy-3-chloro-2-(4-nitrophenoxy)naphthalene

A mixture of the whole 9 g of this 3-chloro-1,4-dihydroxy-2-(4-nitrophenoxy)naphthalene [prepared as described in step (a) above], 6.6 g of acetic anhydride, 7 g of pyridine and 150 ml of benzene was then stirred at room temperature for 20 hours. At the end of this time, the reaction mixture was poured into a mixture of ice and 15 ml of 2N aqueous hydrochloric acid and extracted with benzene. The extract was washed with water and dried over anhydrous sodium sulfate. The solvent was then removed by distillation under reduced pressure, to give 7.8 g of 1,4-diacetoxy-3-chloro-2-(4-nitrophenoxy)naphthalene.

Thin layer chromatography:
Rf value: 0.40;
Adsorbent: silica gel plate No. 5715 (Merck);
Developing solvent: benzene.

18(c)
1,4-Diacetoxy-2-(4-aminophenoxy)-3-chloronaphthalene

Following a procedure similar to that described in Preparation 1(c), 8.5 g of the 1,4-diacetoxy-3-chloro-2-(4-nitrophenoxy) naphthalene [prepared as described in step (b) above] were hydrogenated under an atmosphere of hydrogen and in the presence of 1.7 g of 10% palladium-on-charcoal in 200 ml of tetrahydrofuran at room temperature for 5 hours, to give 8.3 g of 1,4-diacetoxy-2-(4-aminophenoxy)-3-chloronaphthalene as an oily substance.

Thin layer chromatography:
Rf value: 0.10;
Adsorbent: silica gel plate No. 5715 (Merck);
Developing solvent: a 10:0.3 by volume mixture of benzene and ethyl acetate.

18 (d) Butyl 2-bromo-3-[4-(1,4-diacetoxy-3-chloro-2-naphthyloxy)phenyl]propionate Following a procedure similar to that described in Preparation 1(d), 8.3 g of 1,4-diacetoxy-2-(4-aminophenoxy)-3-chloronaphthalene [prepared as described in step (c) above] were arylated using 15 g of a 47% w/v aqueous solution of hydrobromic acid, 1.9 g of sodium nitrate, 27 g of butyl acrylate and 0.5 g of cupric bromide, to give 5.8 g of the title compound as a pale yellow oil.

Nuclear Magnetic Resonance Spectrum (CDCl$_3$, partial) δ ppm:
0.91 (3H, triplet, J=7 Hz);
3.19 (1H, doublet of doublets, J=14 & 7 Hz);
3.41 (1H, doublet of doublets, J=14 & 8 Hz);
4.34 (1H, doublet of doublets, J=8 & 7 Hz).

PREPARATION 19

2-(2,3,4,5-Tetramethoxy-6-methylphenyl)ethanol

19 (a) 1-Allyl-2,3,4,5-tetramethoxy-6-methylbenzene

A catalytic amount of iodine was added to a suspension of 975 mg of magnesium in 20 ml of tetrahydrofuran, and the resulting mixture was warmed up to about 45° C. to give rise to a white turbidity. A solution of 10.61 g of 2,3,4,5-tetramethoxy-6-methylbromobenzene in 30 ml of tetrahydrofuran was then added to the mixture, after which it was heated at about 45° C. for several minutes. The mixture was then stirred at room temperature for 30 minutes, after which 3.47 ml of allyl bromide were added dropwise to the mixture; it was then stirred at room temperature for 2 hours. At the end of this time, the reaction mixture was mixed with a saturated aqueous solution of ammonium chloride and then extracted with ethyl acetate. The solvent was removed from the extract by distillation under reduced pressure, and the residue thus obtained was purified by column chromatography through silica gel, using a 10:1 by volume mixture of hexane and ethyl acetate as the eluent, to give 7.98 g of the title compound as an oil.

Nuclear Magnetic Resonance Spectrum (CDCl$_3$) δ ppm: (only the signals due to an allyl group are reported)
about 3.4 (2H, multiplet);
4.85–5.05 (2H, multiplet);
5.8–6.0 (1H, multiplet).

19(b)
2-(2,3,4,5-Tetramethoxy-6-methylphenyl)acetaldehyde 109 mg of osmium tetroxide were added to a solution of 7.98 of 1-allyl-2,3,4,5-tetramethoxy-6-methylbenzene [prepared as described in step (a) above] in a mixture of 300 ml of dioxane and 100 ml of water, and the resulting mixture was stirred at room temperature for 10 minutes. An aqueous solution of 35.6 g of sodium periodate was then added dropwise, and the mixture was stirred at room temperature for 2 hours. At the end of this time, the reaction mixture was freed from the dioxane by evaporation under reduced pressure, and the resulting concentrate was poured into a saturated aqueous solution of sodium chloride, after which it was extracted with diisopropyl ether. The solvent was then removed from the extract by distillation under reduced pressure, and the resulting residue was purified by column chromatography through silica gel, using a gradient elution method with mixtures of hexane and ethyl acetate ranging from 8:1 to 5:1 by volume as the eluent, to give 4.64 g of the title compound.

Nuclear Magnetic Resonance Spectrum (CDCl$_3$) (partial) δ ppm:
 3.71 (2H, doublet, J=2 Hz);
 9.68 (1H, triplet, J=2 Hz).

19 (c) 2-(2,3,4,5-Tetramethoxy-6-methylphenyl)ethanol 5.38 g of 2-(2,3,4,5-tetramethoxy-6-methylphenyl)acetaldehyde [prepared as described in step (b)-above] were dissolved in 60 ml of ethanol and reduced using 400 mg of sodium borohydride at 0° C. 150 ml of a saturated aqueous solution of sodium chloride were then added to the reaction mixture, and the mixture was extracted with ethyl acetate. The extract was dried over anhydrous magnesium sulfate and concentrated to dryness by evaporation under reduced pressure, to give a crude product. This crude product was then purified by column chromatography through silica gel, using a gradient elution method with mixtures of hexane and ethyl acetate ranging from 5:1 to 2:1 by volume as the eluent, to give 5.27 g of the title compound as a colorless oil.

Nuclear Magnetic Resonance Spectrum (CDCl$_3$) δ ppm:
 2.19 (3H, singlet);
 2.90 (2H, triplet, J=7 Hz);
 3.75 (2H, triplet, J=7 Hz);
 3.78 (3H, singlet);
 3.85 (3H, singlet);
 3.90 (3H, singlet);
 3.91 (3H, singlet).

PREPARATION 20

1,4-Dimethoxy-2-naphthylmethanol

20(a) Methyl 1,4-dimethoxy-2-naphthoate 20.7 g of anhydrous potassium carbonate were added to a solution of 5.1 g of 1,4-dihydroxy-2-naphthoic acid in 50 ml of dimethylformamide, and 28.4 g of methyl iodide were added dropwise to the resulting mixture, after which it was stirred for 19 hours. At the end of this time, the reaction mixture was poured into water, and the aqueous mixture was neutralized with 3N aqueous hydrochloric acid and extracted with ethyl acetate. The extract was dried over anhydrous sodium sulfate, and the solvent was removed by distillation under reduced pressure. The resulting residue was purified by column chromatography through silica gel, using a 10:1 by volume mixture of hexane and ethyl acetate as the eluent, to give 5.45 g of the title compound as a yellow oil.

Thin layer chromatography:
 Rf value: 0.24;
 Adsorbent: silica gel plate No. 5715 (Merck);
 Developing solvent: a 10:1 by volume mixture of hexane and ethyl acetate.

20 (b) 1,4-Dimethoxy-2-naphthylmethanol

A solution of 5.32 g of methyl 1,4-dimethoxy-2-naphthoate [prepared as described in step (a) above] in 15 ml of tetrahydrofuran was added dropwise to a suspension of 0.98 g of lithium aluminum hydride in 15 ml of tetrahydrofuran, whilst ice-cooling. The resulting mixture was then stirred at room temperature for 1 hour, after which 20 ml of a saturated aqueous solution of ammonium chloride was added. The precipitate which formed was filtered off, and then the product was extracted with ethyl acetate. The extract was dried over anhydrous sodium sulfate and then concentrated by evaporation under reduced pressure, to give 3.97 g of the title compound as a pale yellow solid, melting at 63°-66° C.

Nuclear Magnetic Resonance Spectrum (CDCl$_3$) δ ppm:
 3.92 (3H, singlet);
 4.00 (3H, singlet);
 4.89 (2H, singlet);
 6.82 (1H, singlet);
 7.45-7.6 (2H, multiplet);
 8.04 (1H, doublet, J=8 Hz);
 8.23 (1H, doublet, J=9 Hz).

PREPARATION 21

2-(1,4-Dimethoxy-2-naphthyl)ethanol

21(a) 1,4,-Dimethoxy-2-naphthylmethyltriphenylphosphonium chloride

A solution of 4.73 g of 1,4-dimethoxy-2-naphthylmethyl chloride (prepared as described in Preparation 29) and 6.29 g of triphenylphosphine in 50 ml of dry acetonitrile was heated under reflux for 2 hours. At the end of this time, the reaction mixture was freed from the solvent by distillation under reduced pressure, and the resulting crystalline residue was washed with diethyl ether and air-dried, to give 7.36 g of the title compound as a white powder, melting at 244°-246° C. (with decomposition).

21(b) 1,4-Dimethoxy-2-vinylnaphthalene 50 ml of a 10% aqueous solution of sodium hydroxide were added dropwise, with stirring, to a mixture of 7.36 g of 1,4-dimethoxy-2-naphthylmethyltriphenylphosphonium chloride [prepared as described in step (a) above] and 75 ml of a 30% V/v aqueous solution of formaldehyde, and the resulting mixture was stirred for 1 hour. At the end of this time, the reaction mixture was neutralized with 3N aqueous hydrochloric acid, after which it was extracted with ethyl acetate. The extract was dried over anhydrous sodium sulfate, and the solvent was removed by distillation under reduced pressure. The resulting residue was purified by column chromatography through silica gel, using a 24:1 by volume mixture of hexane and ethyl acetate as the eluent, to give 2.45 g of the title compound as a pale yellow oil.

Thin layer chromatography:
 Rf value: 0.53;
 Adsorbent: silica gel plate No. 5715 (Merck);
 Developing solvent: a 24:1 by volume mixture of hexane and ethyl acetate.

21 (c) 2- (1,4-Dimethoxy-2-naphthyl)ethanol 1.61 g of titanium tetrachloride were added to a mixture of 0.65 g of sodium borohydride and 20 ml of dry ethylene glycol dimethyl ether, and the resulting mixture was stirred at room temperature for 1 hour. A solution of 1.83 g of 1,4-dimethoxy-2-vinylnaphthalene [prepared as described in step (b) above] in 40 ml of dry ethylene glycol dimethyl ether was then added dropwise to the resulting mixture, and the mixture was stirred for 21 hours. At the end of this time, the reaction mixture was poured into water, after which it was extracted with ethyl acetate. The extract was dried over anhydrous sodium sulfate, and the solvent was removed by distillation under reduced pressure. The resulting residue was purified by column chromatography through silica gel, using a 1:2 by volume mixture of hexane and ethyl acetate as the eluent, to give 0.40 g of the title compound as a colorless oil.

Nuclear Magnetic Resonance Spectrum (CDCl$_3$) δ ppm:
3.07 (2H, triplet, J=7 Hz);
3.91 (3H, singlet);
3.93 (2H, triplet, J=7 Hz);
3.98 (3H, singlet);
6.63 (1H, singlet);
7.4–7.6 (2H, multiplet);
8.02 (1H, doublet, J=8 Hz);
8.22 (1H, doublet, J=8 Hz).

PREPARATION 22

3-(1,4-Dimethoxy-2-naphthyl)propanol

22(a) 1,4-Dimethoxy-2-formylnaphthalene 4.18 g of manganese dioxide were added to a solution of 0.87 g of 1,4-dimethoxy-2-naphthylmethanol (prepared as described in Preparation 20) in 10 ml of methylene chloride, and the resulting mixture was stirred at room temperature for 6.5 hours. At the end of this time, the reaction mixture was filtered to remove inorganic materials, and the filtrate was dried over anhydrous sodium sulfate, after which the solvent was removed by distillation under reduced pressure. The resulting crystalline residue was washed with hexane and air-dried, to give 0.57 g of the title compound as pale yellow needles, melting at 120°–123° C.

Thin layer chromatography:
Rf value: 0.44;
Adsorbent: silica gel plate No. 5715 (Merck);
Developing solvent: a 4:1 by volume mixture of hexane and ethyl acetate.

22 (b) Methyl trans-3-(1,4-dimethoxy-2-naphthyl)acrylate 0.40 g of trimethyl phosphonoacetate was added to a suspension of 0.10 g of sodium hydride (as a 55% w/w dispersion in mineral oil, which had previously been washed with dry hexane) in 6 ml of dimethyl sulfoxide, and the resulting mixture was stirred for 20 minutes. 0.43 g of 1,4-dimethoxy-2-formylnaphthalene [prepared as described in step (a) above] was then added, whilst ice-cooling, to the mixture, and the mixture was stirred for 1 hour. At the end of this time, the reaction mixture was poured into water, after which it was extracted with ethyl acetate. The extract was dried over anhydrous sodium sulfate, and the solvent was removed by distillation under reduced pressure. The residue was purified by column chromatography through silica gel, using a 4:1 by volume mixture of hexane and ethyl acetate as the eluent, to give 0.47 g of the title compound as a pale yellow oil.

Thin layer chromatography:
Rf value: 0.42;
Adsorbent: silica gel plate No. 5715 (Merck);
Developing solvent: a 4:1 by volume mixture of hexane and ethyl acetate.

22 (c) Methyl 3-(1,4-dimethoxy-2 -naphthyl)propionate 0.47 g of methyl trans-3-(1,4-dimethoxy-2-naphthyl)acrylate [prepared as described in step (b) above] was dissolved in 20 ml of methanol and hydrogenated under an atmosphere of hydrogen and in the presence of 0.20 g of 10% w/w palladium-on-charcoal, to give 0.41 g of the title compound as a colorless oil.

Thin layer chromatography:
Rf value: 0.66;
Adsorbent: silica gel plate No. 5715 (Merck);
Developing solvent: a 3:2 by volume mixture of hexane and ethyl acetate.

22 (d) 3-(1,4-Dimethoxy-2-naphthyl)propanol

Following a procedure similar to that described in Preparation 20(b), but using 0.41 g of methyl 3-(1,4-dimethoxy-2-naphthyl)propionate [prepared as described in step (c) above], 68 mg of lithium aluminum hydride and 6 ml of tetrahydrofuran, 0.34 g of the title compound was obtained as a colorless oil.

Nuclear Magnetic Resonance Spectrum (CDCl$_3$) δ ppm:
1.85–2.0 (2H, multiplet);
2.91 (2H, triplet, J=7 Hz);
3.58 (2H, triplet, J=6 Hz );
3.91 (3H, singlet);
3.98 (3H, singlet);
6.60 (1H, singlet);
7.4–7.6 (2H, multiplet);
8.01 (1H, doublet, J=8 Hz);
8.21 (1H, doublet, J=8 Hz).

PREPARATION 23

4-(1,4-Dimethoxy-2-naphthyl)butanol 23 (a) 4-(1,4-Dimethoxy-2-naphthyl)butyronitrile A solution of 5.08 g of 3-(1,4-dimethoxy-2-naphthyl)propyl iodide (prepared as described in Preparation 30), and 0.70 g of sodium cyanide in 60 ml of dry dimethyl sulfoxide was stirred at 60° C. (external temperature) for 80 minutes. At the end of this time, the reaction mixture was cooled and poured into water, after which it was extracted with ethyl acetate. The extract was dried over anhydrous sodium sulfate and the solvent was removed by distillation under reduced pressure. The resulting residue was purified by column chromatography through silica gel, using a 4:1 by volume mixture of hexane and ethyl acetate as the eluent, to give 3.36 g of the title compound as a colorless oil.

Thin layer chromatography:
Rf value: 0.19;
Adsorbent: silica gel plate No. 5715 (Merck);
Developing solvent: a 7:1 by volume mixture of hexane and ethyl acetate.

23 (b) 4-(1,4-Dimethoxy-2-naphthyl)butyraldehyde 20 ml of a 1.0M hexane solution of diisobutylaluminum hydride were added at −70° C. to a solution of 3.36 g of 4-(1,4-dimethoxy-2-naphthyl)butyronitrile [prepared as described in step (a) above] in 100 ml of dry methylene chloride, and the resulting mixture was stirred for 2 hours. At the end of this time, water was added to the reaction mixture, and the insoluble materials were filtered off with the aid of a Celite (trade name) filter aid. The methylene chloride layer which separated was dried over anhydrous sodium sulfate, and the solvent was removed by distillation under reduced pressure, to give 2.96 g of the title compound as a colorless oil.

Thin layer chromatography:
Rf value: 0.19;
Adsorbent: silica gel plate No. 5715 (Merck);
Developing solvent: a 7:1 by volume mixture of hexane and ethyl acetate.

23 (c) 4-(1,4-Dimethoxy-2-naphthyl)butanol

Following a procedure similar to that described in Preparation 1(c), but using 2.96 g of 4-(1,4-dimethoxy-2-naphthyl)butyraldehyde [prepared as described in step (b) above], 0.87 g of sodium borohydride and 80 ml of ethanol, 2.84 g of the title compound were obtained as a colorless oil.

Nuclear Magnetic Resonance Spectrum (CDCl$_3$) δ ppm:
1.6–1.95 (4H, multiplet);
2.83 (2H, triplet, J=8 Hz);
3.71 (2H, triplet, J=7 Hz);
3.87 (3H, singlet);
3.97 (3H, singlet);
6.61 (1H, singlet);
7.4–7.6 (2H, multiplet);
8.01 (1H, doublet, J=8 Hz);
8.20 (1H, doublet, J=8 Hz).

PREPARATION 24

3-(2,5-Dimethoxy-3,4,6-trimethylphenyl)propyl iodide 2.13 ml of methanesulfonyl chloride were added dropwise at 0° C. to a mixture of 5.47 g of 3-(2,5-dimethoxy-3,4,6-trimethylphenyl)propanol, 4.8 ml of triethylamine and 50 ml of methylene chloride, and the resulting mixture was stirred for 30 minutes. At the end of this time, the reaction mixture was mixed with a mixture of 50 ml of ice-water and 50 ml of 10% w/v aqueous hydrochloric acid. The organic layer which separated was washed with a saturated aqueous solution of sodium hydrogencarbonate and with a saturated aqueous solution of sodium chloride, in that order, after which it was dried over anhydrous magnesium sulfate. The solvent was then removed by distillation under reduced pressure, the residue was dissolved in 100 ml of acetone, and 6.88 g of sodium iodide were added to the resulting mixture. The reaction mixture was then stirred at 50° C. for 2 hours, after which the solvent was removed by distillation under reduced pressure. The residue was mixed with 100 ml of a saturated aqueous solution of sodium thiosulfate, after which it was extracted with ethyl acetate. The extract was freed from the solvent by distillation under reduced pressure, and the residue was purified by column chromatography through silica gel, using a 10:1 by volume mixture of hexane and ethyl acetate as the eluent, to give 7.7 g of the title compound as an oil.

Nuclear Magnetic Resonance Spectrum (CDCl$_3$) δ ppm:
2.00 (2H, quintet, J=7 Hz);
2.17 (6H, singlet);
2.23 (3H, singlet);
2.71 (2H, doublet of doublets, J=7 Hz);
3.27 (2H, triplet, J=7 Hz);
3.64 (3H, singlet);
3.67 (3H, singlet)

PREPARATIONS 25 TO 31

Following a procedure similar to that described in Preparation 24 above, compounds of formula (I-8):

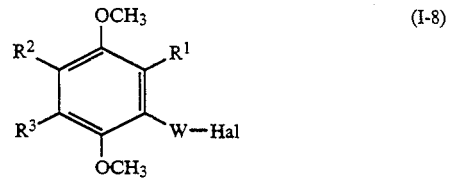

(in which $R^1$, $R^2$, $R^3$, W and Hal are as defined in Table 8) were obtained from the corresponding hydroxy compounds by replacing the hydroxy group of the hydroxy compound by the halogen atom shown in Table 8. The abbreviations are as given for Table 4, and, in Preparations 29, 30 and 31, $R^2$ and $R^3$ together represent the group shown under their columns.

TABLE 8

| Preparation No. | $R^1$ | $R^2$ | $R^3$ | W | Hal |
|---|---|---|---|---|---|
| 25 | Me | Me | Me | —CH$_2$— | Br |
| 26 | Me | Me | Me | —(CH$_2$)$_4$— | I |
| 27 | Me | MeO | MeO | —CH$_2$— | Br |
| 28 | Me | MeO | MeO | —(CH$_2$)$_3$— | I |
| 29 | H | —CH=CH—CH=CH— | | —CH$_2$— | Cl |
| 30 | H | —CH=CH—CH=CH— | | —(CH$_2$)$_3$— | I |
| 31 | Me | —CH=CH—CH=CH— | | —CH$_2$— | Cl |

Nuclear Magnetic Resonance spectrum of the compound of Preparation 25, δ ppm, CDCl$_3$ (partial due to W):
4.66 (2H, singlet).

Nuclear Magnetic Resonance spectrum of the compound of Preparation 26, δ ppm, CDCl$_3$ (partial due to W):
1.50–1.70 (2H, multiplet);
1.85–2.00 (2H, multiplet);
2.63 (2H, doublet of doublets, J=8 Hz);
3.24 (2H, triplet, J=7 Hz).

Nuclear Magnetic Resonance spectrum of the compound of Preparation 27, δ ppm, CDCl$_3$ (partial due to W):
4.61 (2H, singlet).

Nuclear Magnetic Resonance spectrum of the compound of Preparation 28, δ ppm, CDCl$_3$ (partial due to W):
1.90–2.10 (2H, multiplet);
2.67 (2H, doublet of doublets, J=8 Hz);
3.26 (2H, triplet, J=7 Hz).

Nuclear Magnetic Resonance spectrum of the compound of Preparation 29, δ ppm, CDCl$_3$ (partial due to W):
4.85 (2H, singlet).

Nuclear Magnetic Resonance spectrum of the compound of Preparation 30, δ ppm, CDCl$_3$ (partial due to W):
2.22 (2H, quintet, J=7 Hz);
2.90 (2H, triplet, J=7 Hz );
3.26 (2H, triplet, J=7 Hz).

Nuclear Magnetic Resonance spectrum of the compound of Preparation 31, δ ppm, CDCl$_3$ (partial due to W):
4.92 (2H, singlet).

PREPARATION 32

5-(4-Hydroxybenzyl)-3-triphenylmethylthiazolidine-2,4-dione

32(a) 5-(4-Acetoxybenzylidene)thiazolidine-2,4-dione

A mixture comprising 200 g of p-hydroxybenzaldehyde, 229 g of thiazolidine-2,4-dione, 280 g of sodium acetate and 660 ml of dimethylacetamide was stirred at 150° for 1 hour. It was then cooled, and 540 ml of dimethylacetamide and 370 ml of acetic anhydride were added to the reaction mixture. The resulting mixture was then stirred at 50° C. for 1.5 hours, after which it was poured into water. The solid which precipitated was collected by filtration, washed with water, and dried in vacuo, to give 390 g of the title compound.

32 (b) 5-(4-Acetoxybenzyl)thiazolidine-2,4-dione 2.0 g of 5-(4-acetoxybenzylidene)thizaolidine-2,4-dione [prepared as described in step (a) above] was dissolved in 80 ml of acetic acid and was hydrogenated under an atmosphere of hydrogen at atmospheric pressure at 90° C. for 5 hours in the presence of 2.0 g of 10% w/w palladium-on-charcoal. At the end of this time, the catalyst was filtered off, and the filtrate was diluted with toluene. The acetic acid solvent was then removed by distillation as a toluene azeotrope. The crystals which separated out on adding toluene and hexane to the concentrate were collected by filtration and dried to give 1.8 g of the title compound.

32(c) 5-(4-Acetoxybenzyl)-3-triphenylmethylthiazolidine-2,4-dione 3.43 g of triethylamine were added to a solution of 9.0 g of 5-(4-acetoxybenzyl)thiazolidine-2,4-dione [prepared as described in step (b) above] in 70 ml of methylene chloride, and a solution of 9.45 g of triphenylmethyl chloride in 30 ml of methylene chloride was added dropwise to the resulting mixture. The mixture was then stirred at room temperature for 1 hour, after which it was allowed to stand overnight at the same temperature. At the end of this time, the reaction mixture was mixed with water and ethyl acetate, and the organic layer was separated, washed with a saturated aqueous solution of sodium chloride, and dried over anhydrous sodium sulfate. The crystals which separated out on distilling off the solvent under reduced pressure, were washed with a mixture of hexane and ethyl acetate and dried, to give 7.86 g of the title compound.

32(d) 5-(4-Hydroxybenzyl)-3-triphenylmethylthiazolidine-2,4-dione

A solution of 2.99 g of a 28% w/v methanolic solution of sodiumamethoxide in 10 ml of methanol was added dropwise, whilst ice-cooling, to a solution of 7.86 g of 5-(4-acetoxybenzyl)-3-triphenylmethyl-thiazolidine-2,4-dione [prepared as described in step (c) above] in 70 ml of toluene, and the resulting mixture was stirred at room temperature for 1 hour, after which it was allowed to stand overnight at the same temperature. The pH of the reaction mixture was then adjusted to a value of 4 by the addition of 1N aqueous hydrochloric acid, and the mixture was extracted with ethyl acetate. The extract was washed with water and dried over anhydrous sodium sulfate. The solvent was then removed by distillation under reduced pressure, and the crystals which appeared in the residue were collected, washed with hexane and dried, to give 6.0 g of the title compound.

We claim:

1. Compounds of formula (I):

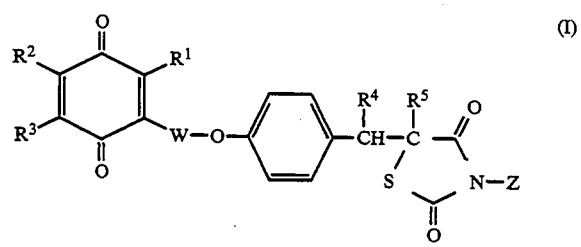

wherein:
- $R^1$ represents an alkyl group having from 1 to 5 carbon atoms;
- $R^2$ and $R^3$ are the same or different and each represents an alkyl group having from 1 to 5 carbon atoms or an alkoxy group having from 1 to 5 carbon atoms, or

- $R^2$ and $R^3$ together form a benzene ring which is unsubstituted or which is substituted by at least one substituent selected from the group consisting of substituents A, defined below, and, when $R^2$ and $R^3$ together form said benzene ring, $R^1$ represents a hydrogen atom, a halogen atom or an alkyl group having from 1 to 5 carbon atoms;
- $R^4$ and $R^5$ both represent hydrogen atoms, or $R^4$ and $R^5$ together represent a single carbon-carbon bond;
- W represents a single bond or an alkylene group having from 1 to 5 carbon atoms; and
- Z represents a hydrogen atom or a 1/x equivalent of a cation, where x is the charge on the cation; and
- substituents A are selected from the group consisting of alkyl groups having from 1 to 5 carbon atoms, alkoxy groups having from 1 to 5 carbon atoms and halogen atoms.

2. The compound of claim 1, wherein Z represents an alkali metal, one half equivalent of an alkaline earth metal or a basic amino acid.

3. The compound of claim 1, wherein $R^2$ and $R^3$ are the same or different and each represents an alkyl group having from 1 to 5 carbon atoms or an alkoxy group having from 1 to 5 carbon atoms, or $R^2$ and $R^3$ together form an unsubstituted benzene ring, and, when $R^2$ and $R^3$ together form said benzene ring, $R^1$ represents a hydrogen atom, a methyl group or a chlorine atom.

4. The compound of claim 3, wherein $R^2$ and $R^3$ are the same.

5. The compound of claim 1, wherein $R^4$ and $R^5$ each represents a hydrogen atom.

6. The compound of claim 1, wherein W represents an alkylene group having from 1 to 5 carbon atoms.

7. The compound of claim 1, wherein Z represents a hydrogen atom or a sodium atom.

8. The compound of claim 1, wherein:
- $R^1$ represents an alkyl group having from 1 to 5 carbon atoms;
- $R^2$ and $R^3$ are the same or different and each represents an alkyl group having from 1 to 5 carbon atoms or an alkoxy group having from 1 to 5 carbon atoms, or $R^2$ and $R^3$ together form an unsubstituted benzene ring, and, when $R^2$ and $R^3$ together form said benzene ring, $R^1$ represents a hydrogen atom, a methyl group or a chlorine atom;
$R^4$ and $R^5$ each represents a hydrogen atom;
W represents an alkylene group having from 1 to 5 carbon atoms; and
Z represents a hydrogen atom or a sodium atom.

9. The compound of claim 1, wherein $R^2$ and $R^3$ are the same or different and each represents an alkyl group having from 1 to 5 carbon atoms.

10. The compound of claim 1, wherein W represents an alkylene group having 2 to 4 carbon atoms.

11. The compound of claim 1, wherein:
$R^1$ represents an alkyl group having from 1 to 5 carbon atoms;
$R^2$ and $R^3$ are the same or different and each represents an alkyl group having from 1 to 5 carbon atoms;
$R^4$ and $R^5$ each represents a hydrogen atom;
W represents an alkylene group having 2 to 4 carbon atoms; and
Z represents a hydrogen atom or a sodium atom.

12. The compound of claim 1, wherein $R^1$, $R^2$ and $R^3$ each represents a methyl group.

13. The compound of claim 1, wherein W represents an ethylene or trimethylene group.

14. The compound of claim 1, wherein:
$R^1$, $R^2$ and $R^3$ each represents a methyl group;
$R^4$ and $R^5$ each represents a hydrogen atom;
W represents an ethylene or trimethylene group; and
Z represents a hydrogen atom or a sodium atom.

15. The compound of claim 1, which is 5-[4-(3,5,6-trimethyl-1,4-benzoquinon-2-ylmethoxy)benzyl]-thiazolidi ne-2,4-dione sodium salt.

16. The compound of claim 1, which is 5-{4-[2-(3,5,6-trimethyl-1,4-benzoquinon-2-yl)ethoxy]benzy l}thiazolidine-2,4-dione.

17. The compound of claim 1, which is 5-{4-[3-(3,5,6-trimethyl-1,4-benzoquinon-2-yl)propoxy]benz yl} thiazolidine-2,4-dione.

18. The compound of claim 1, which is 5-{4-[3-(3,5,6-trimethyl-1,4-benzoquinon-2-yl)propoxy]benz yl} thiazolidine-2,4-dione sodium salt.

19. The compound of claim 1, which is 5-{4-[4-(3,5,6-trimethyl-1,4-benzoquinon-2-yl)butoxy]benzy l}thiazolidine-2,4-dione.

20. A pharmaceutical composition for the treatment or prophylaxis of diabetes or hyperlipemia, which comprises an effective amount of an active compound in admixture with a pharmaceutically acceptable carrier or diluent, wherein said active compound is selected from the group consisting of compounds of formula (I), as claimed in claim 1.

21. The composition of claim 20, wherein:
$R^1$ represents an alkyl group having from 1 to 5 carbon atoms;
$R^2$ and $R^3$ are the same or different and each represents an alkyl group having from 1 to 5 carbon atoms or an alkoxy group having from 1 to 5 carbon atoms, or $R^2$ and $R^3$ together form an unsubstituted benzene ring, and, when $R^2$ and $R^3$ together form said benzene ring, $R^1$ represents a hydrogen atom, a methyl group or a chlorine atom;
$R^4$ and $R^5$ each represents a hydrogen atom;
W represents an alkylene group having from 1 to 5 carbon atoms; and
Z represents a hydrogen atom or a sodium atom.

22. The composition of claim 20, wherein:
$R^1$ represents an alkyl group having from 1 to 5 carbon atoms;
$R^2$ and $R^3$ are the same or different and each represents an alkyl group having from 1 to 5 carbon atoms;
$R^4$ and $R^5$ each represents a hydrogen atom;
W represents an alkylene group having 2 to 4 carbon atoms; and
Z represents a hydrogen atom or a sodium atom.

23. The composition of claim 20, wherein:
$R^1$, $R^2$ and $R^3$ each represents a methyl group;
$R^4$ and $R^5$ each represents a hydrogen atom;
W represents an ethylene or trimethylene group; and
Z represents a hydrogen atom or a sodium atom.

24. The composition of claim 20, wherein said active compound is selected from the group consisting of:
5-[4-(3,5,6-trimethyl-1,4-benzoquinon-2-ylmethoxy)-benzyl]thiazolidine-2,4-dione sodium salt;
5-{4-[2-(3,5,6-trimethyl-1,4-benzoquinon-2-yl)ethoxy]benzyl}thiazolidine-2,4-dione;
5-{4-[3-(3,5,6-trimethyl-1,4-benzoquinon-2-yl)propoxy]benzyl}thiazolidine-2,4-dione;
5-{4-[3-(3,5,6-trimethyl-1,4-benzoquinon-2-yl)propoxy]benzyl}thiazolidine-2,4-dione sodium salt; and
5-{4-[4-(3,5,6-trimethyl-1,4-benzoquinon-2-yl)butoxy]benzyl}thiazolidine-2,4-dione.

25. A method for the treatment or prophylaxis of diabetes or hyperlipemia in a meal, which method comprises administering to said mammal an effective amount of an active compound, wherein said active compound is selected from the group consisting of compounds of formula (I), as claimed in claim 1.

26. The method of claim 25, wherein:
$R^1$ represents an alkyl group having from 1 to 5 carbon atoms;
$R^2$ and $R^3$ are the same or different and each represents an alkyl group having from 1 to 5 carbon atoms or an alkoxy group having from 1 to 5 carbon atoms, or $R^2$ and $R^3$ together form an unsubstituted benzene ring, and, when $R^2$ and $R^3$ together form said benzene ring, $R^1$ represents a hydrogen atom, a methyl group or a chlorine atom;
$R^4$ and $R^5$ each represents a hydrogen atom;
W represents an alkylene group having from 1 to 5 carbon atoms; and
Z represents a hydrogen atom or a sodium atom.

27. The method of claim 25, wherein:
$R^1$ represents an alkyl group having from 1 to 5 carbon atoms;
$R^2$ and $R^3$ are the same or different and each represents an alkyl group having from 1 to 5 carbon atoms;
$R^4$ and $R^5$ each represents a hydrogen atom;
W represents an alkylene group having 2 to 4 carbon atoms; and
Z represents a hydrogen atom or a sodium atom.

28. The method of claim 25, wherein:
$R^1$, $R^2$ and $R^3$ each represents a methyl group;
$R^4$ and $R^5$ each represents a hydrogen atom;
W represents an ethylene or trimethylene group; and
Z represents a hydrogen atom or a sodium atom.

29. The method of claim 25, wherein said active compound is selected from the group consisting of:
5-[4-(3,5,6-trimethyl-1,4-benzoquinon-2-ylmethoxy)-benzyl]thiazolidine-2,4-dione sodium salt;
5-{4-[2-(3,5,6-trimethyl-1,4-benzoquinon-2-yl)ethoxy]benzyl}thiazolidine-2,4-dione;
5-{4-[3-(3,5,6-trimethyl-1,4-benzoquinon-2-yl)propoxy]benzyl}thiazolidine-2,4-dione;
5-{4-[3-(3,5,6-trimethyl-1,4-benzoquinon-2-yl)propoxy]benzyl}thiazolidine-2,4-dione sodium salt; and
5-{4-[4-(3,5,6-trimethyl-1,4-benzoquinon-2-yl)butoxy]benzyl}thiazolidine-2,4-dione.

* * * * *

UNITED STATES PATENT AND TRADEMARK OFFICE
CERTIFICATE OF CORRECTION

PATENT NO. : 5,338,855
DATED : August 16, 1994
INVENTOR(S) : Yoshioka et al

It is certified that error appears in the above-indentified patent and that said Letters Patent is hereby corrected as shown below:

Column 42, line 25, (claim 25) before "which" delete "meal" and insert --mammal --.

Signed and Sealed this

Twenty-fourth Day of October, 1995

BRUCE LEHMAN

Attest:

Attesting Officer

Commissioner of Patents and Trademarks